US010492780B2

(12) United States Patent
Gross et al.

(10) Patent No.: US 10,492,780 B2
(45) Date of Patent: Dec. 3, 2019

(54) SELF-RETAINING VARIABLE LOOP SUTURES

(75) Inventors: Jeffrey M. Gross, Vancouver (CA); Lev Drubetsky, Coquitlam (CA); William L. D'Agostino, Hamden, CT (US); William L. Hunter, Vancouver (CA)

(73) Assignees: Ethicon, Inc., Somervlle, NJ (US); Ethicon LLC, Guaynabo, PR (US)

( * ) Notice: Subject to any disclaimer, the term of this patent is extended or adjusted under 35 U.S.C. 154(b) by 150 days.

(21) Appl. No.: 13/429,150

(22) Filed: Mar. 23, 2012

(65) Prior Publication Data

US 2012/0245629 A1    Sep. 27, 2012

Related U.S. Application Data

(60) Provisional application No. 61/466,924, filed on Mar. 23, 2011.

(51) Int. Cl.
*A61B 17/06* (2006.01)
*A61B 17/04* (2006.01)
*A61B 17/00* (2006.01)

(52) U.S. Cl.
CPC .... *A61B 17/06166* (2013.01); *A61B 17/0485* (2013.01); *A61B 2017/00004* (2013.01); *A61B 2017/044* (2013.01); *A61B 2017/0417* (2013.01); *A61B 2017/0462* (2013.01); *A61B 2017/0464* (2013.01);
(Continued)

(58) Field of Classification Search
CPC .......... A61B 17/06166; A61B 17/0485; A61B 2017/00004; A61B 2017/0475; A61B 2017/0477; A61B 2017/06176; A61B 2017/0496; A61B 2017/0417; A61B 2017/044; A61B 2017/0462; A61B 2017/0464; A61B 17/06195; A61B 17/06; A61B 2017/06052; A61B 2017/06057; A61B 17/0401; A61B 2017/0412;
(Continued)

(56) References Cited

U.S. PATENT DOCUMENTS

| 709,392 A | 9/1902 | Brown |
| 733,723 A | 7/1903 | Lukens |

(Continued)

FOREIGN PATENT DOCUMENTS

| BE | 1014364 | 9/2003 |
| CA | 2309844 | 12/1996 |

(Continued)

OTHER PUBLICATIONS

US 8,663,276 B2, 03/2014, Leung et al. (withdrawn)
(Continued)

*Primary Examiner* — David C Eastwood

(57) ABSTRACT

A suture having a first end for penetrating tissue, an elongated suture body having a periphery; a plurality of retainers on the periphery, and a second end having a variable loop of variable circumference, wherein the variable loop includes a fixed loop slidably engaging the elongated body for slidingly varying the circumference of the variable loop, and wherein the first end may pass through the variable loop to secure tissue as an anchor, the anchor preventing movement of the suture in the direction of deployment of the first end.

20 Claims, 7 Drawing Sheets

(52) U.S. Cl.
CPC ............. *A61B 2017/0475* (2013.01); *A61B 2017/0477* (2013.01); *A61B 2017/0496* (2013.01); *A61B 2017/06176* (2013.01)

(58) Field of Classification Search
CPC .... A61B 2017/0414; A61B 2017/0427; A61B 2017/0461
USPC ........ 606/228, 232, 139, 146, 148, 213, 222
See application file for complete search history.

(56) References Cited

U.S. PATENT DOCUMENTS

| | | | |
|---|---|---|---|
| 816,026 A | 3/1906 | Meier | |
| 879,758 A | 2/1908 | Foster | |
| 1,142,510 A | 6/1915 | Engle | |
| 1,248,825 A | 12/1917 | Dederer | |
| 1,321,011 A | 11/1919 | Cottes | |
| 1,558,037 A | 10/1925 | Morton | |
| 1,728,316 A | 9/1929 | Von Wachenfeldt | |
| 1,886,721 A | 11/1932 | O'Brien | |
| 2,094,578 A | 10/1937 | Blumenthal et al. | |
| 2,201,610 A | 5/1940 | Dawson, Jr. | |
| 2,232,142 A | 2/1941 | Schumann | |
| 2,254,620 A | 9/1941 | Miller | |
| 2,347,956 A | 5/1944 | Lansing | |
| 2,355,907 A | 8/1944 | Cox | |
| 2,421,193 A | 5/1947 | Gardner | |
| 2,452,734 A | 11/1948 | Costclow | |
| 2,472,009 A | 5/1949 | Gardner | |
| 2,480,271 A | 8/1949 | Sumner | |
| 2,572,936 A | 10/1951 | Kulp et al. | |
| 2,591,063 A | 4/1952 | Goldberg | |
| 2,684,070 A | 7/1954 | Kelsey | |
| 2,736,964 A | 3/1956 | Lieberman | |
| 2,779,083 A | 1/1957 | Enton | |
| 2,814,296 A | 11/1957 | Everett | |
| 2,817,339 A | 12/1957 | Sullivan | |
| 2,866,256 A | 12/1958 | Matlin | |
| 2,910,067 A | 10/1959 | White | |
| 2,928,395 A | 3/1960 | Forbes et al. | |
| 2,988,028 A | 6/1961 | Alcamo | |
| 3,003,155 A | 10/1961 | Mielzynski et al. | |
| 3,066,452 A | 12/1962 | Bott et al. | |
| 3,066,673 A | 12/1962 | Bott et al. | |
| 3,068,869 A | 12/1962 | Shelden et al. | |
| 3,068,870 A | 12/1962 | Levin | |
| 3,123,077 A | 3/1964 | Alcamo | |
| 3,166,072 A | 1/1965 | Sullivan, Jr. | |
| 3,187,752 A | 6/1965 | Glick | |
| 3,206,018 A | 9/1965 | Lewis et al. | |
| 3,209,652 A | 10/1965 | Burgsmueller | |
| 3,209,754 A | 10/1965 | Brown | |
| 3,212,187 A | 10/1965 | Benedict | |
| 3,214,810 A | 11/1965 | Mathison | |
| 3,221,746 A | 12/1965 | Noble | |
| 3,234,636 A | 2/1966 | Brown | |
| 3,273,562 A | 9/1966 | Brown | |
| 3,352,191 A | 11/1967 | Crawford | |
| 3,378,010 A | 4/1968 | Codling | |
| 3,385,299 A | 5/1968 | Leroy | |
| 3,394,704 A | 7/1968 | Dery | |
| 3,494,006 A | 2/1970 | Brumlik | |
| 3,522,637 A | 8/1970 | Brumlik | |
| 3,525,340 A | 8/1970 | Gilbert | |
| 3,527,223 A | 9/1970 | Shein | |
| 3,545,608 A | 12/1970 | Berger et al. | |
| 3,557,795 A | 1/1971 | Hirsch | |
| 3,570,497 A | 3/1971 | Lemole | |
| 3,586,002 A | 6/1971 | Wood | |
| 3,608,095 A | 9/1971 | Barry | |
| 3,608,539 A | 9/1971 | Miller | |
| 3,618,447 A | 11/1971 | Goins | |
| 3,646,615 A | 3/1972 | Ness | |
| 3,683,926 A | 8/1972 | Suzuki | |
| 3,700,433 A | 10/1972 | Duhl | |
| 3,716,058 A | 2/1973 | Tanner, Jr. | |
| 3,720,055 A | 3/1973 | de Mestral et al. | |
| 3,748,701 A | 7/1973 | De Mestral | |
| 3,762,418 A | 10/1973 | Wasson | |
| 3,825,010 A | 7/1974 | McDonald | |
| 3,833,972 A | 9/1974 | Brumlik | |
| 3,845,641 A | 11/1974 | Waller | |
| 3,847,156 A | 11/1974 | Trumble | |
| 3,889,322 A | 6/1975 | Brumlik | |
| 3,918,455 A | 11/1975 | Coplan | |
| 3,922,455 A | 11/1975 | Brumlik | |
| 3,941,164 A | 3/1976 | Musgrave | |
| 3,963,031 A | 6/1976 | Hunter | |
| 3,977,937 A | 8/1976 | Candor | |
| 3,980,177 A | 9/1976 | McGregor | |
| 3,981,051 A | 9/1976 | Brumlik | |
| 3,981,307 A | 9/1976 | Borysko | |
| 3,985,138 A | 10/1976 | Jarvik | |
| 3,990,144 A | 11/1976 | Schwartz | |
| 4,006,747 A | 2/1977 | Kronenthal | |
| 4,008,303 A | 2/1977 | Glick et al. | |
| 4,027,608 A | 6/1977 | Arbuckle | |
| 4,043,344 A | 8/1977 | Landi | |
| 4,052,988 A | 10/1977 | Doddi et al. | |
| D246,911 S | 1/1978 | Bess, Jr. et al. | |
| 4,069,825 A | 1/1978 | Akiyama | |
| 4,073,298 A | 2/1978 | Le Roy | |
| 4,075,962 A | 2/1978 | Mabry | |
| 4,098,210 A | 7/1978 | Wright | |
| 4,137,921 A | 2/1979 | Okuzumi et al. | |
| 4,182,340 A | 1/1980 | Spencer | |
| 4,186,239 A | 1/1980 | Mize et al. | |
| 4,198,734 A | 4/1980 | Brumlik | |
| 4,204,541 A | 5/1980 | Kapitanov | |
| 4,204,542 A | 5/1980 | Bokros et al. | |
| 4,259,959 A | 4/1981 | Walker | |
| 4,278,374 A | 7/1981 | Wolosianski | |
| 4,300,424 A | 11/1981 | Flinn | |
| 4,311,002 A | 1/1982 | Hoffmann et al. | |
| 4,313,448 A | 2/1982 | Stokes | |
| 4,316,469 A | 2/1982 | Kapitanov | |
| 4,317,451 A | 3/1982 | Cerwin et al. | |
| 4,372,293 A | 2/1983 | Vijil-Rosales | |
| 4,428,376 A | 1/1984 | Mericle | |
| 4,430,998 A | 2/1984 | Harvey | |
| 4,434,796 A | 3/1984 | Karapetian | |
| 4,449,298 A | 5/1984 | Patz | |
| 4,454,875 A | 6/1984 | Pratt et al. | |
| 4,467,805 A | 8/1984 | Fukuda | |
| 4,490,326 A | 12/1984 | Beroff et al. | |
| 4,492,075 A | 1/1985 | Faure | |
| 4,493,323 A | 1/1985 | Albright et al. | |
| 4,505,274 A | 3/1985 | Speelman | |
| 4,510,934 A | 4/1985 | Batra | |
| 4,531,522 A | 7/1985 | Bedi et al. | |
| 4,532,926 A | 8/1985 | O'Holla | |
| 4,535,772 A | 8/1985 | Sheehan | |
| 4,548,202 A | 10/1985 | Duncan | |
| 4,553,544 A | 11/1985 | Nomoto et al. | |
| 4,610,250 A | 9/1986 | Green | |
| 4,610,251 A | 9/1986 | Kumar | |
| 4,635,637 A | 1/1987 | Schreiber | |
| 4,637,380 A | 1/1987 | Orejola | |
| 4,653,486 A | 3/1987 | Coker | |
| 4,669,473 A | 6/1987 | Richards et al. | |
| 4,676,245 A | 6/1987 | Fukuda | |
| 4,689,882 A | 9/1987 | Lorenz | |
| 4,702,250 A | 10/1987 | Ovil et al. | |
| 4,712,553 A | 12/1987 | MacGregor | |
| 4,719,917 A | 1/1988 | Barrows | |
| 4,741,330 A | 5/1988 | Hayhurst | |
| 4,750,910 A | 6/1988 | Takayanagi et al. | |
| 4,776,337 A | 10/1988 | Palmaz | |
| 4,832,025 A | 5/1989 | Coates | |
| 4,841,960 A | 6/1989 | Garner | |
| 4,865,026 A | 9/1989 | Barrett | |
| 4,873,976 A | 10/1989 | Schreiber | |
| 4,887,601 A | 12/1989 | Richards | |
| 4,895,148 A | 1/1990 | Bays et al. | |

(56) References Cited

U.S. PATENT DOCUMENTS

| | | |
|---|---|---|
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,089,012 A | 2/1992 | Prou |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A * | 6/1992 | Wilk et al. .............. 606/232 |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,178,629 A * | 1/1993 | Kammerer ......... A61B 17/0469 606/148 |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,234,445 A * | 8/1993 | Walker .............. A61B 17/0469 606/139 |
| 5,242,457 A | 9/1993 | Akopov et al. |
| 5,246,441 A | 9/1993 | Ross et al. |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,466,241 A | 11/1995 | Leroy et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,546,957 A | 8/1996 | Heske |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A * | 5/1997 | Loeser ................ A61B 17/06 128/898 |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| D386,583 S | 11/1997 | McFerragamo et al. |
| 5,676,675 A | 11/1997 | Grice |
| 5,683,417 A * | 11/1997 | Cooper ................ A61B 17/04 606/223 |

(56) References Cited

U.S. PATENT DOCUMENTS

| | | |
|---|---|---|
| D387,161 S | 12/1997 | McFerragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |
| 5,779,719 A | 7/1998 | Klein et al. |
| 5,782,864 A | 7/1998 | Lizardi |
| 5,807,403 A | 9/1998 | Boyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | Locicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,475,229 B1 | 11/2002 | Pagedas |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |

(56) References Cited

U.S. PATENT DOCUMENTS

| | | |
|---|---|---|
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,329,271 B2 | 2/2008 | Koyfman et al. |
| 7,371,253 B2 | 5/2008 | Leung et al. |
| 7,381,211 B2 | 6/2008 | Zamierowski |
| 7,513,904 B2 | 4/2009 | Sulamanidze et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,871,425 B2 | 1/2011 | Jones et al. |
| 7,879,072 B2 | 2/2011 | Bonutti et al. |
| 7,919,112 B2 | 4/2011 | Pathak et al. |
| 8,083,770 B2 | 12/2011 | Ruff et al. |
| 8,100,940 B2 | 1/2012 | Leung et al. |
| 8,118,834 B1 | 2/2012 | Goraltchouk et al. |
| 8,216,273 B1 | 7/2012 | Goraltchouk et al. |
| 8,225,673 B2 | 7/2012 | D'Agostino |
| 8,226,684 B2 | 7/2012 | Nawrocki et al. |
| 8,246,652 B2 | 8/2012 | Ruff |
| 8,256,613 B2 | 9/2012 | Kirsch et al. |
| 8,308,761 B2 | 11/2012 | Brailovski et al. |
| 8,402,621 B2 | 3/2013 | Maiorino et al. |
| 8,459,446 B2 | 6/2013 | Kozlowski |
| 8,460,338 B2 | 6/2013 | Goraltchouk et al. |
| 8,641,732 B1 | 2/2014 | Goraltchouk et al. |
| 8,652,170 B2 | 2/2014 | Leung et al. |
| 8,679,158 B2 | 3/2014 | Leung et al. |
| 8,721,664 B2 * | 5/2014 | Ruff .................. A61B 17/04 606/139 |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0051807 A1 | 12/2001 | Grafton |
| 2002/0007218 A1 | 1/2002 | Cauthen |
| 2002/0022861 A1 | 2/2002 | Jacobs |
| 2002/0029011 A1 | 3/2002 | Dyer |
| 2002/0029066 A1 | 3/2002 | Foerster |
| 2002/0077448 A1 | 6/2002 | Antal et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0179718 A1 | 12/2002 | Murokh et al. |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |

(56) References Cited

U.S. PATENT DOCUMENTS

| | | |
|---|---|---|
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |
| 2004/0193217 A1 | 9/2004 | Lubbers et al. |
| 2004/0193257 A1 | 9/2004 | Wu et al. |
| 2004/0230223 A1 | 11/2004 | Bonutti et al. |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 6/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0267531 A1* | 12/2005 | Ruff ........................ A61B 17/04 606/228 |
| 2005/0267532 A1 | 12/2005 | Wu |
| 2005/0277984 A1 | 12/2005 | Long |
| 2005/0283246 A1 | 12/2005 | Cauthen, III et al. |
| 2006/0020272 A1 | 1/2006 | Gildenberg |
| 2006/0030884 A1 | 2/2006 | Young et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0106278 A1* | 5/2006 | Machold et al. ................ 600/37 |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff |
| 2006/0135995 A1 | 6/2006 | Ruff |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0185494 A1 | 8/2007 | Reese |
| 2007/0187861 A1 | 8/2007 | Geneva et al. |
| 2007/0208355 A1 | 9/2007 | Ruff |
| 2007/0208377 A1 | 9/2007 | Kaplan et al. |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1* | 6/2008 | Maiorino ......... A61B 17/06166 606/228 |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |

(56) References Cited

U.S. PATENT DOCUMENTS

| | | |
|---|---|---|
| 2008/0234731 A1 | 9/2008 | Leung et al. |
| 2008/0248216 A1 | 10/2008 | Yeung et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1* | 8/2009 | Cohen et al. ............ 606/232 |
| 2009/0216253 A1 | 8/2009 | Bell et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0318958 A1* | 12/2009 | Ochiai ............ 606/222 |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1* | 3/2010 | Maiorino ............ 606/228 |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0146770 A1 | 6/2010 | Morency et al. |
| 2010/0160961 A1 | 6/2010 | Nawrocki et al. |
| 2010/0163056 A1 | 7/2010 | Tschopp et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298874 A1 | 11/2010 | Leung et al. |
| 2010/0298875 A1 | 11/2010 | Leung et al. |
| 2010/0298876 A1 | 11/2010 | Leung et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0022086 A1 | 1/2011 | D'Agostino et al. |
| 2011/0046668 A1 | 2/2011 | Goraltchouk et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0125188 A1 | 5/2011 | Goraltchouk et al. |
| 2011/0130774 A1 | 6/2011 | Criscuolo et al. |
| 2011/0166597 A1 | 7/2011 | Herrmann et al. |
| 2011/0264138 A1 | 10/2011 | Avelar et al. |
| 2011/0288583 A1 | 11/2011 | Goraltchouk et al. |
| 2011/0319932 A1 | 12/2011 | Avelar et al. |
| 2012/0101522 A1 | 4/2012 | Megaro et al. |
| 2012/0109188 A1 | 5/2012 | Viola |
| 2013/0072971 A1 | 3/2013 | Kim et al. |
| 2013/0103078 A1 | 4/2013 | Longo et al. |
| 2013/0165971 A1 | 6/2013 | Leung et al. |
| 2013/0172931 A1 | 7/2013 | Gross et al. |
| 2013/0180966 A1 | 7/2013 | Gross et al. |
| 2013/0204295 A1 | 8/2013 | Hunter et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0245684 A1 | 9/2013 | Ruff et al. |
| 2013/0317545 A1 | 11/2013 | Gross et al. |

FOREIGN PATENT DOCUMENTS

| | | |
|---|---|---|
| CN | 2640420 | 9/2004 |
| DE | 01810800 | 6/1970 |
| DE | 03227984 | 2/1984 |
| DE | 04302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0513713 | 5/1992 |
| EP | 0428253 | 7/1994 |
| EP | 0632999 | 1/1995 |
| EP | 0513736 | 2/1995 |
| EP | 0464479 | 3/1995 |
| EP | 0464480 | 3/1995 |
| EP | 0576337 A1 | 3/1997 |
| EP | 0576337 B1 | 3/1997 |
| EP | 0574707 | 8/1997 |
| EP | 0612504 | 11/1997 |
| EP | 0558993 | 4/1998 |
| EP | 0913123 | 5/1999 |
| EP | 0916310 | 5/1999 |
| EP | 0664198 | 6/1999 |
| EP | 0960600 | 12/1999 |
| EP | 0705567 | 3/2002 |
| EP | 0673624 | 8/2002 |
| EP | 0839499 | 9/2003 |
| EP | 0755656 | 12/2003 |
| EP | 1075843 | 2/2005 |
| EP | 1525851 | 4/2005 |
| EP | 1532942 | 5/2005 |
| EP | 0826337 | 12/2005 |
| EP | 0991359 | 11/2007 |
| EP | 2036502 | 3/2009 |
| EP | 1948261 | 11/2010 |
| EP | 2245992 | 11/2010 |
| EP | 1726317 | 7/2012 |
| FR | 2619129 | 2/1989 |
| FR | 2693108 | 1/1994 |
| GB | 0267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 54-116419 | 9/1979 |
| JP | 63-288146 | 11/1988 |
| JP | 001113091 | 5/1989 |
| JP | 3-165751 | 7/1991 |
| JP | 4-096758 | 3/1992 |
| JP | 4-266749 | 9/1992 |

(56) References Cited

FOREIGN PATENT DOCUMENTS

| | | |
|---|---|---|
| JP | 9-103477 | 4/1997 |
| JP | 410085225 | 4/1998 |
| JP | H10-286258 A | 10/1998 |
| JP | H10-337291 A | 12/1998 |
| JP | 11-313826 | 11/1999 |
| JP | 011332828 | 12/1999 |
| JP | 2002-059235 | 2/2002 |
| JP | 2003-275217 | 9/2003 |
| JP | 2006-522656 A | 10/2006 |
| JP | 2009-118967 | 6/2009 |
| JP | 2009-247900 A | 10/2009 |
| KR | 10-2005-0072908 A | 7/2005 |
| KR | 6013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 | 1/2006 |
| SU | 1745214 | 7/1992 |
| SU | 1752358 | 8/1992 |
| WO | WO 1996/006565 | 3/1966 |
| WO | WO 1986/000020 | 1/1986 |
| WO | WO 1987/001270 | 3/1987 |
| WO | WO 1988/009157 | 12/1988 |
| WO | WO 1989/005618 | 6/1989 |
| WO | WO 1990/009149 | 8/1990 |
| WO | WO 1990/014795 | 12/1990 |
| WO | WO 1992/022336 | 12/1992 |
| WO | WO 1995/016399 | 6/1995 |
| WO | WO 1995/029637 | 11/1995 |
| WO | WO 1997/000047 | 1/1997 |
| WO | WO 1998/052473 | 11/1998 |
| WO | WO 1998/055031 | 12/1998 |
| WO | WO 1999/021488 | 5/1999 |
| WO | WO 1999/033401 | 7/1999 |
| WO | WO 1999/052478 | 10/1999 |
| WO | WO 1999/059477 | 11/1999 |
| WO | WO 1999/062431 | 12/1999 |
| WO | WO 2000/051658 | 9/2000 |
| WO | WO 2000/051685 | 9/2000 |
| WO | WO 2001/006952 | 2/2001 |
| WO | WO 2001/056626 | 8/2001 |
| WO | WO 2003/001979 | 1/2003 |
| WO | WO 2003/003925 | 1/2003 |
| WO | WO 2003/045255 | 6/2003 |
| WO | WO 2003/077772 | 9/2003 |
| WO | WO 2003/092758 | 11/2003 |
| WO | WO 2003/103733 | 12/2003 |
| WO | WO 2003/103972 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005296 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097556 | 8/2009 |
| WO | WO 2009/149455 A1 | 12/2009 |
| WO | WO 2009/151876 | 12/2009 |
| WO | WO 2010/052007 | 5/2010 |
| WO | WO 2010/107698 A2 | 9/2010 |
| WO | WO 2011/053375 | 5/2011 |
| WO | WO 2011/090628 | 7/2011 |
| WO | WO 2011/139916 | 11/2011 |
| WO | WO 2011/140283 | 11/2011 |

OTHER PUBLICATIONS

International Search Report for PCT/US2012/030441 dated Sep. 27, 2012.
Communication from EPO re: 10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: 10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.
European Search Report for EP10012437 dated Apr. 28, 2011.
European Search Report for EP10186592.1 dated Jan. 19, 2011, 2 pages.
European Search Report for EP10184766 dated Apr. 20, 2011.
Extended European Search Report re: 07015905.8 dated Oct. 23, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
International Search Report for PCT/US1994/09631 dated Dec. 9, 1994.

(56) References Cited

OTHER PUBLICATIONS

International Search Report for PCT/US1998/10478 dated Sep. 23, 1998.
International Search Report for PCT/US2002/20449 dated May 20, 2003.
International Search Report for PCT/US2002/027525 dated Dec. 9, 2002, 3 pages.
International Search Report for PCT/US2003/030424 dated Nov. 1, 2004.
International Search Report for PCT/US2003/030664 dated May 25, 2004.
International Search Report for PCT/2003/030666 dated Dec. 15, 2004.
International Search Report for PCT/US2003/025088 dated Dec. 29, 2003.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2007/074658 dated Jun. 12, 2007, 3 pages.
International Search Report for PCT/US2008/060127 dated Sep. 23, 2008, 5 pages.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report for PCT/US2011/059238 dated May 21, 2012.
International Search Report for PCT/US2012/041001 dated Sep. 26, 2012.
Partial European Search Report re: EP05025816 dated Mar. 20, 2006.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
Singapore Search Report for Singapore Patent Application No. 201103117-6 dated Mar. 8, 2013.
Supplementary European Search Report re: EP98923664 dated Jun. 12, 2001.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: EP03785177 dated May 19, 2009.
Supplementary European Search Report re: 05750101 dated Apr. 7, 2010.
Supplementary European Search Report re: 07017663 dated Nov. 7, 2007.
Bacci, Pier Antonio, "Chirurgia Estetica Mini Invasiva Con Fili Di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Bellin, I. et al., "Polymeric triple-shape materials", Proceedings of the National Academy of Sciences of the United States of America Nov. 28, 2006; 2103(48):18043-18047.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7, pp. 24-35.
Bunnell, S. 'Gig pull-out suture for tendons' J Bone Joint Surg. Am (1954) vol. 36A, No. 4 pp. 850-851.
CCPR Centro De Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED—University of Puerto Rico, Mayaguez May 2005, p. F1-F27.
Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Gross, R.A. et al 'Biodegradable Polymers for the Environment' Science (2002) vol. 297, Issue 5582 pp. 803.
Han, H. et al 'Mating and Piercing Micromechanical Suture for Surface Bonding Applications' (1991) Proceedings of the 1991

(56) References Cited

OTHER PUBLICATIONS

Micro Electro Mechanical Systems (MEMS>91), An Investigation of Micro Structures, Sensors, Actuators, Machines and Robots pp. 253-258.

Ingle, N.P. et al 'Barbed Suture Anchoring Strength: Applicability to Dissimilar Polymeric Materials' College of Textiles, North Carolina State University, 7th World Biomaterials Congress 2004, 1 page.

Ingle, N.P. et al 'Mechanical Performance and Finite Element Analysis of Bi-directional Barbed Sutures' Master of Science in Textile Technology & Management at North Carolina State University Aug. 2003, 126 pages.

Ingle, N.P. et al., "Optimizing the tissue anchoring performance of barbed sutures in skin and tendon tissues", Journal of Biomechanics 43 (2010); pp. 302-309.

Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.

Jennings et al 'A New Technique in primary tendon repair' Surg. Gynecol. Obstet. (1952) vol. 95, No. 5 pp. 597-600.

Jeong, H.E. et al 'A nontransferring dry adhesive with hierarchial polymer nanohairs' PNAS 106 (14) pp. 5639-5644 (2009).

Kaminer, M. et al., "ContourLift™: A New Method of Minimally Invasive Facial Rejuvenation", Cosmetic Dermatology Jan. 2007;20(1):29-35.

Kelch et al., "Shape-memory Polymer Networks from Olio [(ϵ-hydroxycaproate)-co-glycolate]dimethacrylates and Butyl Acrylate with Adjustable Hydrolytic Degradation Rate", Biomacromolecules 2007;8(3):1018-1027.

Khademhosseini, Ali et al., "Nanobiotechnology Drug Delivery and Tissue Engineering", Chemical Engineering Progress 102:38-42 (2006).

Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.

Lendlein, A. et al 'Biodegradable, Elastic Shape-Memory Polymers for Potential Biomedical Applications' (2002) Science vol. 296 pp. 1673-1676.

Lendlein, A. et al 'Shape-Memory Polymers' Agnew Chem. Int. Ed. (2002) vol. 41 pp. 2034-2057.

Leung, J. et al 'Barbed, Bi-directional Medical Sutures: Biomechanical Properties and Wound Closure Efficacy Study' 2002 Society for Biomaterials 28th Annual Meeting Transactions 1 page.

Leung, J. et al 'Barbed, Bi-directional Surgical Sutures' International Conference & Exhibition on Healthcare & Medical Textiles, Jul. 8-9, 2003 pp. 1-8.

Leung, J. et al 'Barbed, Bi-directional Surgical Sutures: In Vivo Strength and Histopathology Evaluations' 2003 Society for Biomaterials 29th Annual Meeting Transactions pp. 100.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Leung, J. et al 'Performance Enhancement of a Knotless Suture via Barb Geometry Modifications' 7th World Biomaterials Congress 2004, 1 page.

Li, Y.Y. et al 'Polymer Replicas of Photonic Porous Silicon for Sensing and Drug Delivery Applications' (2003) Science vol. 299 pp. 2045-2047.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

Madduri, Srinivas, et al., "Neurotrophic factors release from nerve conduits for peripheral axonal regeneration", European Cells and Materials vol. 16; Suppl. 1 (2008), p. 14.

Madhave et al 'A biodegradable and biocompatible gecko-inspired tissue adhesive' PNAS 105(7) pp. 2307-2312 (2008).

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al 'Endovascular AAA Exclusion: Will Stents with Hooks and Barbs Prevent Stent-Graft Migration' Journal Endovascular Surgery (1998) vol. 5 pp. 310-317.

Mansberger et al 'A New Type Pull-Out Wire for Tendon Surgery: A Preliminary Report' Department of Surgery, University I Iospital and University of Maryland School of Medicine, Baltimore, Maryland, Received for Publication May 10, 1951 pp. 119-121.

Martin, D.P. et al 'Medical applications of poly-4-hydroxybutyrate: a strong flexible absorbable biomaterial' Biochemical Engineering Journal vol. 16 (2003) pp. 97-105.

Mason, M.L. 'Primary and Secondary Tendon Suture. A discussion of the significance of technique in tendon surgery' (1940) Surg Gynecol Obstet 70.

McKee, GK 'Metal anastomosis tubes in tendon suture' The Lancet (1945) pp. 659-660.

McKenzie 'An Experimental Multiple Barbed Suture for the Long Flexor Tendons of the Palm and Fingers' The Journal of Bone and Joint Surgery (1967) vol. 49B, No. 3 pp. 440-447.

Middleton and Tipton 'Synthetic Biodegradable Polymers as Medical Devices' (1998) Medical Plastics and Biomaterials Magazine, 9 pages.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Murtha et al., "Evaluation of a Novel Technique for Wound Closure Using a Barbed Suture", Journal of the American Society of Plastic Surgeons 2006; 117(6); 1769-1780.

Nie, Zhihong and Kumacheva, Eugenia, "Patterning surfaces with functional polymers", Nature Materials vol. 7(2008): 277-290.

Paul, Malcolm D., "Bidirectional Barbed Sutures for Wound Closure: Evolution and Applications", Journal of the American College of Certified Wound Specialists (2009) 1, 51-57.

Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.

Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.

Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.

Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.

Paul, Malcolm D., "Using Barbed Sutures in Open/Subperiosteal Midface Lifting", Aesthetic Surgery Journal 2006(26): 725-732.

Potenza, A. 'Tendon Healing Within the Flexor Digital Sheath in the Dog: An Experimental Study' Journal of Bone & Joint Surgery (1962) vol. 44A No. 1 pp. 49-64.

Pulvertaft 'Suture Materials and Tendon Junctures' American Journal of Surgery (1965) vol. 109 pp. 346-352.

Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.

Quill Medical, Inc. 'Quill Medical's Novel-Self-Anchoring Surgical Suture Approved for Sale in Europe' Press Release; Research Triangle Park, N.C. May 10, 2004, 1 page.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Richert, Ludovic, et al., "Surface Nanopatterning to Control Cell Growth", Advanced Materials 2008(15): 1-5.

(56) References Cited

OTHER PUBLICATIONS

Rodeheaver, G.T. et al., "Barbed Sutures for Wound Closure: In Vivo Wound Security, Tissue Compatibility and Cosmesis Measurements", Society for Biomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherrnan, Peter et al., "Sutures as longitudinal guides for the repair of nerve defects—Influence of suture numbers and reconstruction of nerve bifurcations", Restorative Neurology and Neuroscience 23 (2005) 79-85.
Schmid A. et al 'The outspreading anchor cord. A material for arthroscopic suturing of a fresh anterior cruciate ligament rupture' Surgical Clinic of the University of Gottingen (1987) pp. 417-426.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pgs. 281-306.
Sulamanidze, M.A. et al 'Clinical aspects of bloodless facelift using APTOS filaments' A.V. Vishnevsky Institute of Surgery, Bol'shaya Scrpukhovskaya ul, 7, 113811, Moscow, Russia (2002) pp. 24-34.
Sulamanidze, M.A. et al 'Facial lifting with Aptos threads' International Journal of Cosmetic Surgery and Aesthetic Dermatology (2001) No. 4 pp. 1-8.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 19-26.
Sulamanidze, M.A. et al 'Removal of Facial Soft Tissue Ptosis with Special Threads' Dermatol Surg (2002) vol. 28 pp. 367-371.
Sulamanidze, MD, M.A., et al., "Soft tissue lifting in the mid-face: old philosophy, new approach—internal stitching technique (APTOS Needle)", Plastic and Aesthetic Surgery Clinic Total Sharm, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Szarmach, R. et al 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Supplementary European Search Report re: 12760468 dated Jul. 10, 2014.
Australian Office Action, Patent Examination Report No. 1, dated Sep. 30, 2015 for Application No. AU 2012230716, 4 pgs.
Canadian Office Action dated Mar. 5, 2018 for Application No. CA 2,830,961, 4 pgs.
Chinese Office Action, The First Office Action, and Search Report dated Aug. 27, 2015 for Publication No. CN 201280025020.3, 10 pgs.
Chinese Office Action, The Second Office Action, dated Apr. 28, 2016 for Publication No. CN 201280025020.3, 7 pgs.
Europe Exam Report dated Aug. 11, 2015 for Application No. EP 12760468.4, 6 pgs.
Japanese Office Action, Decision of Refusal, dated Aug. 23, 2016 for Application No. JP 2014-501287, 2 pgs.
Japanese Office Action, Decision to Grant a Patent, dated Mar. 14, 2017 for Application No. JP 2014-501287, 3 pgs.
Japanese Office Action, Decision to Grant a Patent, dated Jul. 31, 2018 for Application No. JP 2016-249200, 3 pgs.
Japanese Office Action, Notification of Reasons for Refusal, and Search Report dated Nov. 21, 2017 for Application No. JP 2016-249200, 16 pgs.
Japanese Office Action, Notification of Reasons for Refusal, and Search Report dated Dec. 15, 2015 for Application No. JP 2014-501287, 68 pgs.
International Search Report and Written Opinion dated Sep. 27, 2012 for Application No. PCT/US2012/030441, 5 pages.
International Preliminary Report on Patentability and Written Opinion dated Sep. 24, 2013 for Application No. PCT/US2012/030441, 6 pgs.
Chinese Search Report, Supplementary, dated Aug. 31, 2016 for Application No. CN 201280025020.3, 1 pg.
European Office Action, Decision to Grant, dated Jan. 5, 2017 for Application No. EP 127060468.4, 2 pgs.
Mexican Office Action dated Jul. 28, 2015 for Application No. MX/a/2013/010899, 4 pgs.
Russian Office Action dated Mar. 21, 2016 for Application No. RU 2013147159/14, 3 pgs.
U.S. Appl. No. 61/329,436.
U.S. Appl. No. 61/466,924, filed Mar. 23, 2011, by Gross et al., titled: "Self-Retaining Variable Loop Sutures.".

* cited by examiner

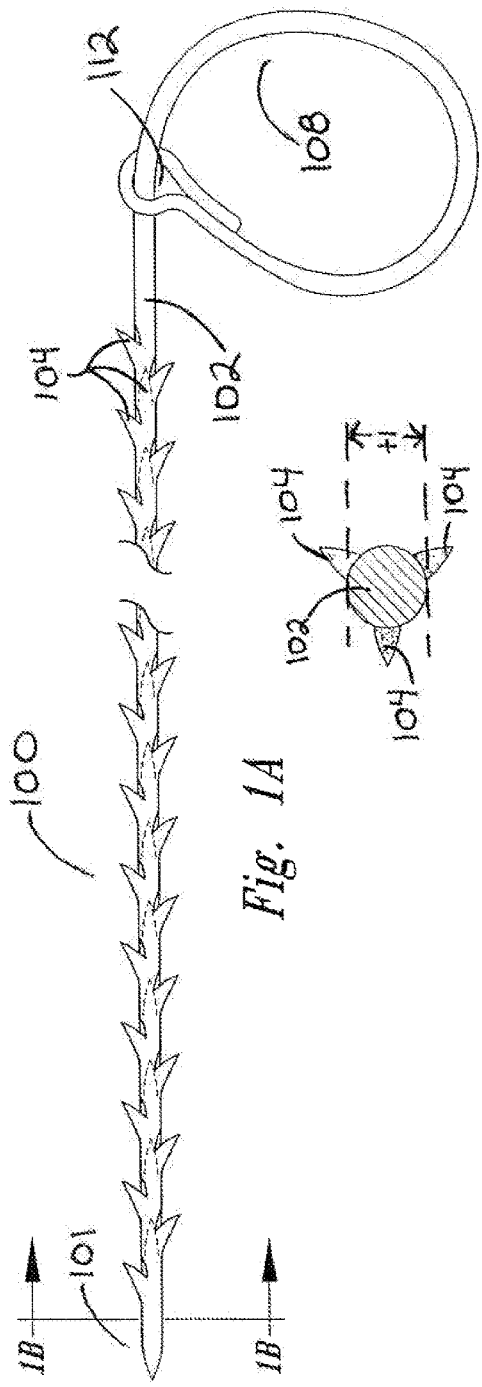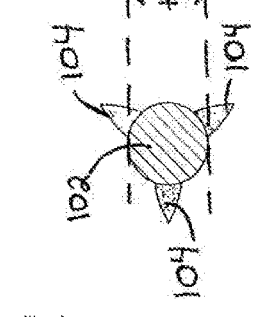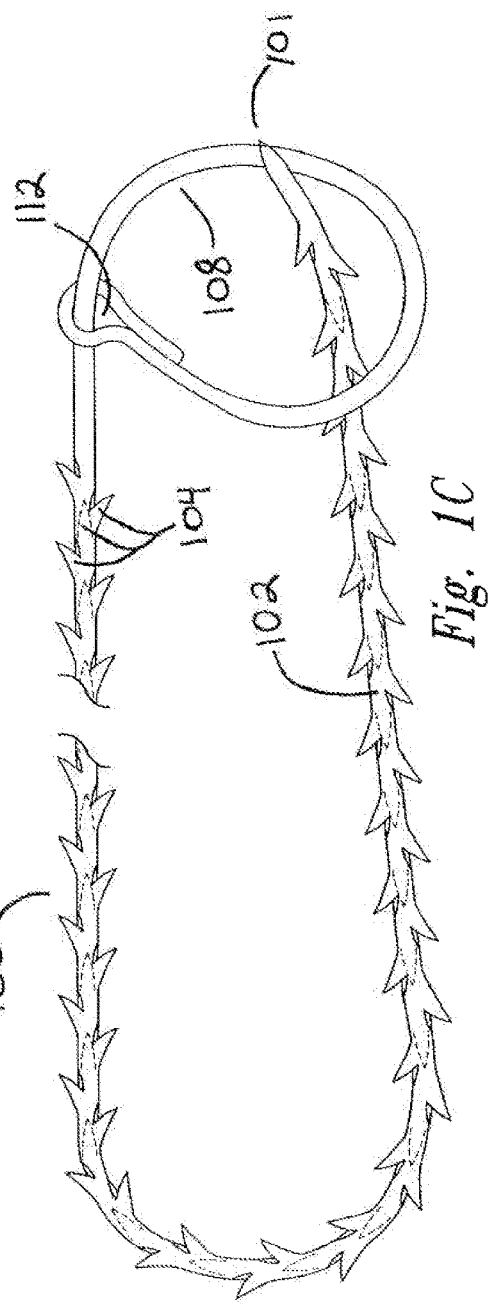

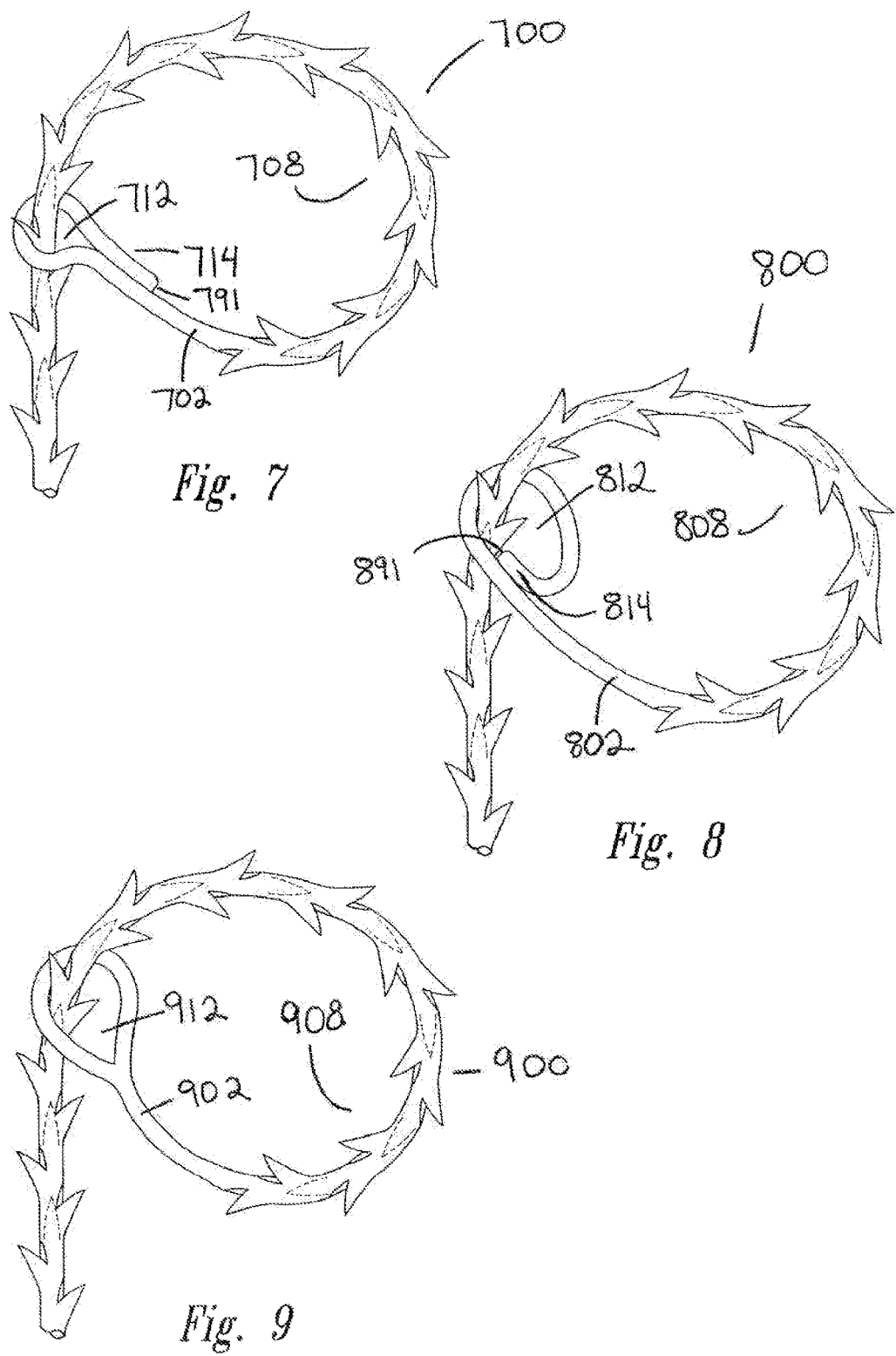

SELF-RETAINING VARIABLE LOOP SUTURES

CROSS-REFERENCE TO RELATED APPLICATION

This application claims the benefit under 35 U.S.C. § 119(e) of U.S. Provisional Patent Application No. 61/466,924, filed Mar. 23, 2011, which application is hereby incorporated by reference in its entirety.

FIELD OF THE INVENTION

The present invention relates generally to sutures, including self-retaining sutures and unidirectional self-retaining sutures, methods of manufacturing the sutures, and their uses in wound repair and surgical procedures.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available; the shape and size of the needle body and the configuration of the needle tip is typically selected based upon the needs of the particular application.

To use an ordinary suture, a suture needle is advanced through the desired tissue on one side of the wound and then through the adjacent side of the wound. The ends of the suture are then brought into proximity to one another and then held together, e.g., by tying a knot in the suture to hold the wound closed. Knot tying takes time and causes a range of complications, including, but not limited to (i) spitting, a condition where the suture, usually a knot, pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatuses for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin). All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points that produce a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and 6,241,747). Although any number of sequential or intermittent configurations of retainers are possible, a common form of self-retaining suture involves a needle at one end of a suture thread which has barbs having tips projecting "away" from the needle. Projecting "away" from the needle means that the tip of the retainer is further away from the needle and the portion of suture comprising the suture may be pulled more easily through tissue in the direction of the needle than in the opposite direction. Examples of various retainer configurations are described, for example, in U.S. Patent Application Publication Nos. 20040060409, issued as U.S. Pat. No. 8,100,940 on Jan. 24, 2012, 20040060410, issued as U.S. Pat. No. 8,795,332 on Aug. 5, 2014, 20080255611, issued as U.S. Pat. No. 8,915,943 on Dec. 23, 2014, and 20100087855, issued as U.S. Pat. No. 8,721,681 on May 13, 2014. In addition, self-retaining sutures having high-density retainer configurations are described in U.S. Patent Application Ser. No. 61/329,436.

Unidirectional self-retaining sutures and their uses have been described in various publications as mentioned above. Various unidirectional sutures with anchors, included anchors having loop elements, have been described in, for example, U.S. Patent Application Publication Nos. 20050267531, 20040060410, issued as U.S. Pat. No. 8,795, 332 on Aug. 5, 2014, 20080255611, issued as U.S. Pat. No. 8,915,943 on Dec. 23, 2014, and 20100063540, issued as U.S. Pat. No. 10,016,196 on Jul. 10, 2018.

SUMMARY

It is desirable in some applications to use unidirectional sutures which, at their trailing ends, have anchors configured to more effectively resist tensions and effectively preclude movement when the suture is deployed in tissue. It is also desirable in some applications to provide unidirectional sutures with anchors which, when deployed in tissue, have a minimal amount of anchor material entering the tissue as well as a minimal amount of anchor material remaining outside the tissue. Thus, it is desirable to provide improved unidirectional self-retaining sutures which have enhanced ability to anchor into the surrounding tissue, enhanced tissue holding capabilities, enhanced maximum load, and enhanced clinical performance.

The present invention provides improved unidirectional self-retaining sutures which have enhanced ability to anchor into the surrounding tissue, enhanced tissue holding capabilities, enhanced maximum load, and enhanced clinical performance.

In some embodiments of the present invention there is provided a self-retaining suture having a first end for penetrating tissue, an elongated suture body having a periphery, a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end, and a second end having a variable loop of variable circumference. The variable loop includes a fixed loop slidably engaging the elongated body so that the circumference of the variable loop may be changed by sliding the fixed loop along the elongated body, and the first end may pass through the variable loop to secure tissue as an anchor, the anchor preventing movement of the suture in the direction of deployment of the first end.

In some of these embodiments, at least one of the retainers of the first plurality may differ in configuration from other retainers of the first plurality.

In some of these embodiments, the cross section of the elongated suture body may be non-circular. In some embodiments in which the elongated suture body has a non-circular cross sections the cross section may be polygonal.

In some of these embodiments, the first end is adapted to penetrate tissue, while in other of these embodiments the first end is attached to a needle.

In some of these embodiments, the suture may have a surface feature on at least some of the periphery of the elongated body between the fixed loop and the first plurality of retainers, wherein the surface feature resists the sliding of the fixed loop over the surface feature. In some embodiments including surface features, the surface feature is disposed at least in the circumference of the variable loop.

In some embodiments having surface features, the suture feature may include roughening, dimpling, corrugations, ridges, or other textures, while in other such embodiments, the surface feature may include a second plurality of retainers which are oriented away from the first end and thus provide resistance to the sliding of the fixed loop over them. In some of those embodiments in which the surface features include a second plurality of retainers, at least some of the retainers of the second plurality may differ in configuration from retainers of the first plurality.

In some embodiments of the invention, the fixed loop has an inner transverse length which is at least about the same as the transverse length of the suture cross section, and may be up to ten times the transverse length of the suture cross section. In some of these embodiments, the inner transverse length of the fixed loop may be up to four times the transverse length of the suture cross section, while in other of these embodiments it may be up to three times the transverse length of the suture cross section. In yet other of these embodiments, the inner transverse length of the fixed loop may be about one-and-a-half times the transverse length of the suture cross section to about ten times transverse length of the suture cross section, while in others it may be about one-and-a-half times the transverse length of the suture cross section to about four times transverse length of the suture cross section. In yet others, it may be about twice the transverse length of the suture cross section to about three times the transverse length of the suture cross section.

In some embodiments of the invention, the fixed loop may include a grasp engagement element, or a visible or tactile marking.

In some embodiments of the present invention there is provided a self-retaining suture having a first end for penetrating tissue; an elongated suture body having a periphery and a cross section, the cross section having a transverse length; a first plurality of retainers on the periphery of the elongated body which are oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a variable loop of variable circumference. The variable loop includes a fixed loop slidably engaging the elongated body so that the circumference of the variable loop may be changed by sliding the fixed loop along the elongated body, and the first end may pass through the variable loop to secure tissue as a third, anchoring loop in tissue, the anchoring loop preventing movement of the suture in the direction of deployment of the first end.

In some embodiments of the present invention there is provided a self-retaining suture having a first end for penetrating tissue; an elongated suture body having a periphery and a cross section, the cross section having a transverse length; a first plurality of retainers on the periphery of the elongated body which are oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a slip knot, the slip knot including a loop of variable circumference so that the circumference of the loop may be changed by sliding the slip knot, and the first end may pass through the loop to secure tissue as an anchor for preventing movement of the suture in the direction of deployment of the first end.

In some embodiments of the present invention there is provided a self-retaining suture including a first end for penetrating tissue; an elongated suture body having a periphery and a cross section, the cross section having a transverse length; a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; and a second end having a slip knot, the slip knot including a loop of variable circumference. Sliding the slip knot causes the circumference of the loop to change, and the first end may pass through the loop to secure tissue, thereby creating an anchoring loop in the tissue for preventing movement of the suture in the direction of deployment of the first end.

In some embodiments of the present invention there is provided a self-retaining suture that includes a first end for penetrating tissue; an elongated suture body having a periphery and a cross section, the cross section having a transverse length (tl); a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; and a second end having a variable loop of variable circumference, wherein the variable loop includes a fixed loop having an inner transverse length (TL) and slidably engaging the elongated body, so that the circumference of the loop may be changed by sliding the slip knot. The ratio of TL:tl is about 1:1 to about 10:1. The first end may pass through the variable loop to secure tissue as an anchor for preventing movement of the suture in the direction of deployment of the first end.

In any embodiments of the self-retaining suture of the invention, the suture may additionally include a therapeutic agent.

The present invention yet further provides clinical methods and procedures enabled by such improved self-retaining sutures of small diameter.

In one embodiment there is provided a method of suturing tissue, the method comprising (a) providing a suture thread attached to a suture needle, a portion of the suture thread forming a loop having an adjustable circumference; (b) threading the needle through the loop; and (c) deploying the needle through tissue of a patient and approximating the tissue with the suture thread. Optionally, one or more of the following statements may further described this embodiment: the loop comprises suture thread and a fixed loop, the fixed loop having an opening through which the suture thread passes to thereby form the loop having an adjustable circumference; the fixed loop and any means by which the fixed loop is formed or attached to the suture thread, all lie on a surface of the tissue after the tissue has been completely approximated; the circumference of the loop is adjusted to a desired value prior to threading the needle through the loop; the circumference of the loop is adjusted to a desired value after threading the needle through the loop; the circumference of the loop is adjusted to a desired value in the range of 0.5 to 3 inches; the circumference of the loop is reduced to a desired value; the needle is passed into and then out of tissue at first and second locations, respectively, prior to being threaded through the loop; the suture thread comprises tissue retainers; the suture thread comprises cuts in the suture thread, the cuts forming the tissue retainers where optionally a cut lies in a single plane, or in two planes; a cut into the suture thread provides a barb where the barb is a tissue retainer, and there are a plurality of cuts in the suture thread; tissue retainers are present on a portion of the suture thread that forms the loop having an adjustable circumference; tissue retainers are absent from a portion of the loop having an adjustable circumference.

In another embodiment there is provided a method of anchoring a suture at a location on tissue of a patient, the method comprising: (a) providing a suture thread with an eyelet, the suture thread attached to a suture needle at a deployment end of the suture thread; (b) deploying the suture needle into tissue at the location, and then withdrawing the suture needle from tissue at an exit point; (c) passing the needle through a loop comprising suture thread, the loop having a variable circumference; (d) applying tension to the suture thread by pulling on the deployment end of the suture thread; (e) thereby providing an anchor on top of the tissue, the anchor comprising the eyelet, the loop and a portion of the suture thread, the anchor resisting movement of the suture thread in the direction of the deployment end of the suture thread.

The details of one or more embodiments are set forth in the description below. Other features, objects and advantages will be apparent from the description, the drawings, and the claims.

BRIEF DESCRIPTION OF THE DRAWINGS

Features of the invention, and the nature and various advantages thereof will be apparent from the accompanying drawings and the following detailed description of various embodiments of the invention.

FIGS. 1A and 1C are views of a self-retaining variable loop suture in accordance with an embodiment of the present invention.

FIG. 1B is a cross-sectional view of the suture in FIG. 1A, taken along the line in FIG. 1A that is labeled "1B".

FIG. 7 is a view of the variable loop portion of a self-retaining suture in accordance with a further embodiment of the invention, illustrating a configuration of a fixed loop of that embodiment.

FIG. 8 is a view of the variable loop portion of a self-retaining suture in accordance with another embodiment of the invention, illustrating a configuration of a fixed loop of that embodiment.

FIG. 9 is a view of the variable loop portion of a self-retaining suture in accordance with yet another embodiment of the invention, illustrating a configuration of a fixed loop in of that embodiment.

DETAILED DESCRIPTION

Definitions

Figure 2:
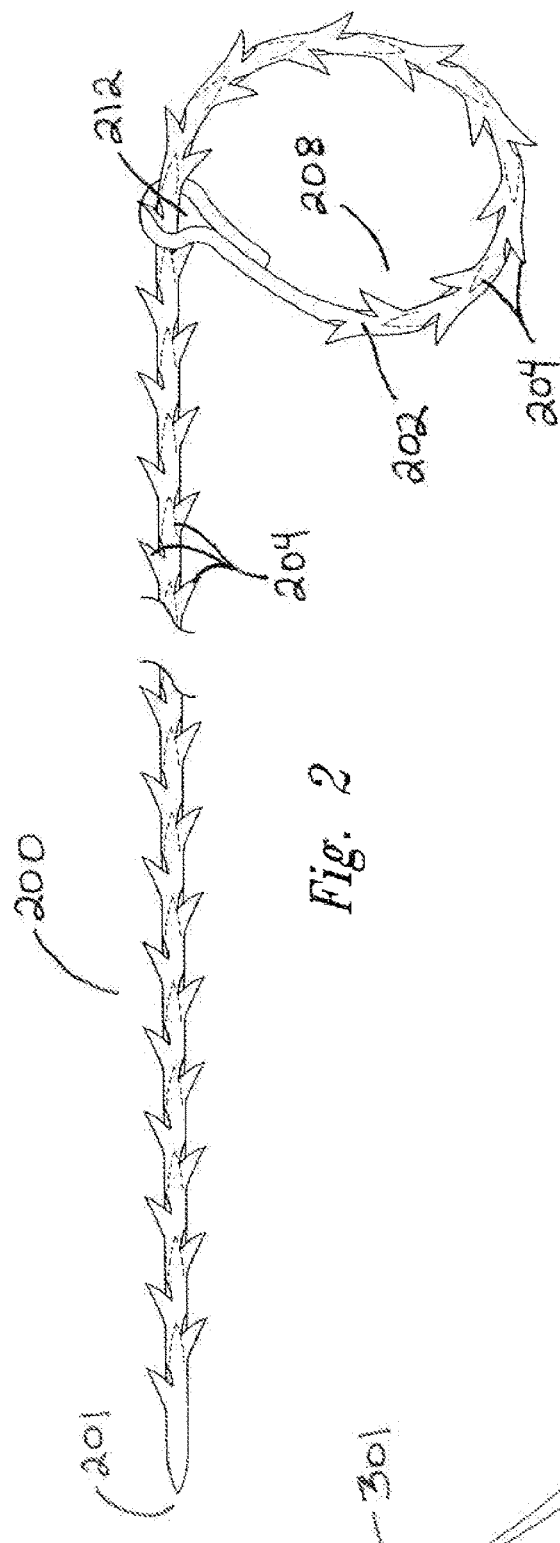
FIG. 2 is a view of a self-retaining variable loop suture in accordance with another embodiment of the present invention.

Definitions of certain terms that may be used herein include the following.

"Armed suture" refers to a suture having a suture needle at the suture deployment end.

"Braided suture" refers to a suture comprising a multi-filamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially mediated by, or performed in, a biological system. "Degradation" refers to a chain scission process by which a polymer chain is cleaved into bloomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™[glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, now abandoned, 20040024169, issued as U.S. Pat. No. 7,026,437 on Apr. 11, 2006, and 20040116620, issued as U.S. Pat. No. 7,070,858 on Jul. 4, 2006. Sutures made from degradable suture material lose tensile strength as the material degrades.

Medical device" or "implant" refers to any object placed in the body for the purpose of restoring physiological function, reducing/alleviating symptoms associated with disease, and/or repairing/replacing damaged or diseased organs and tissues. While normally composed of biologically compatible synthetic materials (e.g., medical-grade stainless steel, titanium and other metals: polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopaedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.).

"Monofilament suture" refers to a suture comprising a monofilamentary suture thread.

"Needle attachment" refers to the attachment of a needle to a suture requiring same for deployment into tissue, and can include methods such as crimping, swaging, using adhesives, and so forth. The point of attachment of the suture to the needle is known as the swage.

"Needle diameter" refers to the diameter of a suture deployment needle at the widest point of that needle. While the term "diameter" is often associated with a circular periphery, it is to be understood herein to indicate a cross-sectional dimension associated with a periphery of any shape. The dimension is the longest dimension between two points on the periphery of the shape, i.e., the distance between the two points on the periphery that are the furthest from one another.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are particularly suitable for applications in which the suture is meant to remain permanently or is meant to be physically removed from the body.

"Retainer configurations" refers to configurations of tissue retainers and can include features such as size, shape, surface characteristics, and so forth. These are sometimes also referred to as "barb configurations".

"Self-retaining suture" refers to a suture that does not require a knot or anchor on at least one of its ends in order to maintain its position into which it is deployed during a surgical procedure. These may be monofilament sutures or braided sutures, and are positioned in tissue in two stages, namely deployment and affixation, and include at least one tissue retainer.

"Self-retaining system" refers to a self-retaining suture together with means for deploying the suture into tissue. Such deployment means include, without limitation, suture needles and other deployment devices as well as sufficiently rigid and sharp ends on the suture itself to penetrate tissue.

"Suture deployment end" refers to an end of the suture to be deployed into tissue. A deployment means such as a suture needle may be located at the suture deployment end, or the suture thread may be formed into a sufficiently sharp and rigid structure so as to penetrate tissue on its own, where this sharp and rigid structure is located at the suture deployment end of the suture.

"Suture diameter" refers to the diameter of the body of the suture when viewed in cross-section. While the term "diameter" is often associated with a circular periphery, it is to be understood herein to indicate a cross-sectional dimension (or distance, or length) associated with a periphery of any shape. For a non-circular shape, the diameter is the longest distance between any two points on the periphery of the cross section, which may also be referred to as the cross-sectional distance. The cross-sectional shape of the suture body or thread is viewed at a location along the suture where there are either no barbs, or the barbs that are present are pushed against the suture body so that they are flush with the surface of the suture body. In one embodiment, the suture body or thread has a generally circular cross-sectional shape. While the suture body may have a circular or generally circular cross-sectional shape, the cross-sectional shape may be non-circular, e.g., it may be polygonal, e.g., 3- (triangular), 4-, 5- or 6-sided (hexagonal) sided. The cross section of the suture body may have an oval, an ellipsoid, an oblong, or a semi-circular appearance. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. Under the USP nomenclature system, the actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0. It is to be understood that a variety of suture lengths may be used with the sutures described herein.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging whereby the suture material is inserted into a channel at the blunt end of the needle which is then deformed to a final shape to hold the suture and needle together. As such, atraumatic needles do not require extra time on site for threading and the suture end at the needle attachment site is smaller than the needle body. In the traumatic needle the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles would be ideal. Suture needles may also be classified according to their point geometry. For example, needles may be (i) "tapered" whereby the needle body is round and tapers smoothly to a point; (ii) "cutting" whereby the needle body is triangular and has sharpened cutting edge on the inside; (iii) "reverse cutting" whereby the cutting edge is on the outside; (iv) "trocar point" or "tapercut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery). Suture needles may also be of several shapes including, (i) straight, (ii) half curved or ski, (iii) ¼ circle, (iv) ⅜ circle, (v) ½ circle, (vi) ⅝ circle, (v) and compound curve. Suturing needles are described, for example, in U.S. Pat. Nos. 6,322,581 and 6,214,030 (Mani, Inc., Japan); and U.S. Pat. No. 5,464,422

(W. L. Gore, Newark, Del.); and U.S. Pat. Nos. 5,941,899; 5,425,746; 5,306,288 and 5,156,615 (US Surgical Corp., Norwalk, Conn.); and U.S. Pat. No. 5,312,422 (Linvatec Corp., Largo, Fla.); and U.S. Pat. No. 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Suture thread" refers to the filamentary body component of the suture, and, for sutures requiring needle deployment, does not include the suture needle. The suture thread may be monofilamentary, i.e., formed of a single filament, or multifilamentary, i.e., formed from a combination of two or more filaments, e.g., three filaments arranged in a braided fashion. The terms "filament" and "filamentary" are used in their ordinary sense, to refer to a long thin structure, and therefore in many instances herein the suture thread is also identified as the elongated body or elongated suture body, where these terms are interchangeable. The filamentous suture thread has a length that is many times its diameter, and in various embodiments the suture thread has a length that is at least 5 times, or at least 10 times, or at least 20 times, or at least 30 times, or at least 40 times, or at least 50 times the diameter of the thread. Indeed, the length of the suture thread may even be at least 100 times the diameter of the thread. In addition to being filamentous, the suture thread is highly flexible. In other words, the thread will bend in any direction as the surgeon moves the suture through the tissue of the patient. The thread may have some memory of its storage condition, for example, if the thread has been stored for a long period of time in a wound-up circular form, it may tend to return to that form even after it has been released from its storage container and unwound. However, the thread is nevertheless going to follow the needle to which it is attached along any path which the needle makes through and around tissue or a wound. The thread can therefore be described as flexible, or pliable. Stated another way, any two adjacent segments of suture thread may be placed, relative to one another, at any angle from essentially or very near to 0 (where the two segments are folded back upon one another) to 180 degrees (where the two segments follow in tandem along a single straight line). The suture thread has a length, where that length is typically at least 5 inches, or at least 10 inches, or at least 15 inchers, or at least 20 inches. The suture thread will typically have two ends, which may be described as a deployment end and/or a trailing end. In such a case, the deployment end of the suture thread is that end which will first enter tissue, usually being adjacent to a needle, while the trailing end of a suture thread would be that end of the thread which is not the deployment end.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects achieve a downward pull on this tissue and the underlying ligaments, and fat descends into the plane between the superficial and deep facial fascia, thus allowing facial tissue to sag. Face-lift procedures are designed to lift these sagging tissues, and are one example of a more general class of medical procedure known as a tissue elevation procedure. More generally, a tissue elevation procedure reverses the appearance change that results from gravitation effects over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Tissue retainer", or simply "retainer", refers to a suture element having a retainer body projecting from the suture body and a retainer end adapted to penetrate tissue; an example of a tissue retainer is a barb. Each retainer is adapted to resist movement of the suture in a direction other than the direction in which the suture is deployed into the tissue by the clinician, by being oriented substantially to the deployment direction (that is, they lie flat when pulled in the deployment direction, and open or "fan out" when pulled in a direction contrary to the deployment direction). As the tissue-penetrating end of each retainer points away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from their deployment positions (that is, yielding toward or resting substantially along the suture body), forces the retainer ends to open (or "fan out") from the suture body in a manner that catches and penetrates into the surrounding tissue, and results in tissue being caught between the retainer and the suture body, thereby "anchoring" or affixing the self retaining suture in place.

"Unidirectional suture" refers to a suture having a deployment end, a trailing end, and retainers oriented to the deployment end. The trailing end may be used to prevent the suture from moving out of the tissue in the direction of deployment, either by having a knot tied in it or by being provided with an anchoring element that remains outside the point in the tissue into which the deployment end of the suture was initially inserted. (In contrast, a bidirectional suture has retainers oriented in one direction at one end and retainers oriented in the other direction at the other end. A bidirectional suture is typically armed with a needle at each end of the suture thread. The bidirectional suture may have a retainer-free transitional segment located between the two retainer orientations.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a gunshot, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume of new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

Unidirectional Self-Retaining Sutures

Self-retaining sutures (including barbed sutures) differ from conventional sutures in that they possess numerous tiny tissue retainers (such as barbs) which anchor into the tissue following deployment and resist movement of the suture in a direction opposite to that in which the retainers face, thereby eliminating the knots that would otherwise have to be tied, around the deployment end of the suture, to affix adjacent tissues together (a "knotless" closure) at the site where the suture deployment end exits from the tissue. By eliminating knot tying, associated complications are eliminated, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops in the tissue that are created by knots tied during a surgical procedure may lead to ischemia (they create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time). Thus, knotless sutures not only allow patients to experience an improved clinical outcome, but they also save time and costs associated with extended surgeries and follow-up treatments.

Self-retaining sutures for wound closure also result in better approximation of the wound edges, evenly distribute the tension along the length of the wound (reducing areas of tension that can break or lead to ischemia), decrease the bulk of suture material remaining in the wound (by eliminating knots tied during procedures) and reduce spitting (the extrusion of suture material—typically knots—through the surface of the skin. All of these features are thought to reduce scarring, improve cosmesis, and increase wound strength relative to wound closures effected with plain sutures or staples.

Self-retaining sutures also lend themselves to a variety of specialized indications; for example, they are suitable for tissue elevation procedures where tissue is moved from its previous location and repositioned into a new anatomical location (this is typically performed in cosmetic procedures where "drooping" tissue is elevated and fixed in a more "youthful" position; or where "out-of-position" tissue is moved back to its correct anatomical location). Such procedures include facelifts, brow lifts, breast lifts, buttocks lifts, and so forth.

Unidirectional self-retaining sutures and their uses have been described in various publications mentioned above. While the segment of suture thread adjacent to the deployment end of a unidirectional self-retaining suture is provided with tissue retainers for preventing slippage of the suture in a direction substantially opposite the direction of deployment, the trailing end may be provided with an anchor to prevent slippage in the deployment direction (and in order to avoid the undesirable potential effects of requiring a knot to be tied during a surgical procedure in the trailing end of a unidirectional suture). Various unidirectional sutures with anchors, included anchors having loop elements, have been described in, for example, U.S. Patent Application Publication Nos. 20050267531, 20040060410, issued as U.S. Pat. No. 8,795,332 on Aug. 5, 2014, 20080255611, issued as U.S. Pat. No. 8,915,943 on Dec. 23, 2014, and 20100063540, issued as U.S. Pat. No. 10,016,196 on Jul. 10, 2018.

Several problems common to existing unidirectional self-retaining sutures having loop anchors can be addressed by the embodiments of this invention. For example, unidirectional sutures featuring fixed loop anchors, such as those described in some of the aforementioned publications, have several disadvantages, the first of which is that the size of the fixed loop should typically be fairly small (that is, not much bigger than the size of the first stitch that the clinician would wish to make with it), which requires the clinician to make some effort (and therefore expend some valuable surgical time) in finding the loop and running the deployment end of the suture through it. Because the suture of the present invention includes a variable loop anchor, the clinician is presented with a large loop through which he or she can easily pass the deployment end of the suture; this is of particular benefit in laparoscopic procedures. Then, when such a suture is pulled through tissue, if the first stitch taken is larger than the longest interior dimension of the fixed loop after the suture body has been drawn through it and tensioned, then the base of the loop (that is, where the loop joins the suture body) can be pulled into the tissue, resulting in potential issues such as those described above in connection with knot-tying. On the other hand, if the first stitch taken is smaller than the longest interior dimension of the fixed loop after the suture body has been drawn through it and tensioned, then excess loop material remains at the tissue site, an axiomatically undesirable condition which could also cause surgical instruments to get caught on the excess material during the procedure. In the case of the present invention, the adjustable nature of the variable loop anchor allows the clinician to avoid these difficulties.

In addition, there are physical issues of loop integrity associated with a fixed loop anchor. For example, issues of fixed loop attachment are avoided by the variable loop suture of the present invention. Where the loop of a fixed loop suture is welded or otherwise attached to the suture body, either as a separate structure joined at its base to the suture or as an end of the suture turned back onto and attached to the suture to create a looped portion, the base of the loop (where it joins the suture body) is the attachment region and is also where the suture is pulled into the tissue. As such, it is subject to tissue drag and the potential for breakage or peeling at the attachment region. While this may be dealt with by increasing the length of the attachment region and/or providing a taper or chamfer, it is avoided entirely by sutures of the present invention as the eyelet of the variable loop will sit superficial to the tissue being approximated, will not need to pass into the tissue, and is not subject to tissue drag. In addition, for sutures of the present invention, the main load when tensioning the tissue is taken by the variable loop as opposed to the eyelet. As a result, the eyelet does not hold the primary tension when seating the first stitch, and the weld length can be shortened thereby reducing local biomaterial effects (inflammation and/or risk of infection) on wound healing.

Unidirectional self-retaining sutures of the present invention are provided with a variable length loop configuration at one end and a deployment end at the other. Wound closure is achieved by starting at one end of the wound containing tissue to be approximated, passing the deployment end through both edges of the tissue, pulling the end of the suture containing the needle through the tissue until the loop segment is near the first edge of tissue, and passing the end with the needle back through the variable loop portion of the device. Tension is pulled until the loop seats on the tissue and the desired hold is achieved. The deployment end is now passed repeatedly through the tissue in a pattern determined by the clinician to best facilitate wound closure starting at the end just seated moving in one direction toward the other terminus of the tissue to be approximated. A "J stitch" can used to complete the process and the needle is removed akin to the procedure used with bi-directional configurations.

Turning now to FIGS. 1A, 1B and 1C, there is illustrated a suture 100 having a deployment end 101 on an elongated body 102 which is alternatively referred to herein as the suture thread, which body (or thread) has a transverse cross-sectional length (the longest transverse dimension on the cross section). This transverse cross-sectional length is illustrated in FIG. 1B, where FIG. 1B is a cross-sectional view of the suture of FIG. 1A, taken along the line in FIG. 1A that is labeled "1B" where this transverse cross-sectional length is denoted by "tl" in FIG. 1*b*, and FIG. 1B also shows the cross section of the suture body 102 and three retainers each identified as 104 which are shown with different darkening to make the point that they not are the same distance away from the viewer located at position 1B. It is to be understood that the cross-sectional shape of the suture is not limited to circular, but may be non-circular as well (such as an ellipse, a triangle, a square, other polygons, etc.).

Continuing with FIGS. 1A to 1C, the body 102 bears a plurality of retainers 104 oriented toward the deployment end 101, and an eyelet 112 through which the suture body passes, thus forming the variable loop 108. The eyelet is in essence a fixed loop, but one that, in tissue, sits outside the tissue into which the suture is deployed. The presence of the variable loop as part of the anchoring structure assures that all of the force exerted on the anchor is not solely exerted on the fixed loop. This is advantageous because the force is therefore distributed over a broader structure, and the fixed loop (eyelet) or portions thereof, e.g., the attachment region as discussed later herein, are not drawn into the tissue. One benefit is that the anchor can more readily be accessed and then cut away from the suture thread, allowing for greater ease in removing the suture thread after it is deemed that the healing process no longer require the presence of the suture. Absent the variable loop, the anchor would be composed solely of the eyelet or the eyelet in combination with a portion of the suture thread that passes through the eyelet but does not form a variable loop. An anchor that is formed solely of a fixed loop, or is formed from a fixed loop in combination with a suture thread passing through the fixed loop but not forming a variable loop, is observed to pinch the tissue at the anchoring point and may lead to undesirable side effects, for example, tissue necrosis. An anchor formed from a fixed loop (eyelet) and a variable loop and a portion of the elongated body (suture thread) provides for less pinching of the tissue and thus less opportunity for undesired tissue necrosis.

As shown in FIG. 1C, the deployment end 101 can be passed through the variable loop 108. As the deployment end 101 continues to be drawn through the variable loop 108, and tension is applied to the suture thread 102 from the direction of the deployment end 101, more and more of the suture thread 102 will be drawn or threaded through the variable loop. In practice, the deployment end 101 will pass through a patient's tissue before it passes through the variable loop 108, and therefore as the suture thread 102 passes through the variable loop 108, the eyelet 112 will be pulled toward the surface of the patient's tissue and will eventually be held firmly on that tissue by the tension or force exerted on the deployment end 101. With continued pulling or force or tension, the circumference of the variable loop will tend to decrease, until such time as the clinician determines that the variable loop has a desired circumference, at which time the clinician will stop pulling on the deployment end and the anchor is thus formed. Thereafter, the clinician will return to sewing the patient's tissue with the now-anchored suture.

As shown in FIGS. 1A and 1C, the region of the suture body along which the plurality of retainers is provided may be greater than the region of the suture body that is used in forming an eyelet. Furthermore, the eyelet does not necessarily contain any retainers, although retainers of a sort may be present in order to assist in gripping the suture body within the eyelet. Retainers may be absent from the variable loop portion of the suture, as shown in FIGS. 1A and 1C, or retainers may be present in this portion of the suture as shown in later figures provided herein.

As can be seen in FIG. 2, suture 200 has retainers 204 on suture body 202, which run along most of the length of the suture body 202 including the variable loop 208 formed from the suture body 202, to approach eyelet 212. As retainers 204 are oriented toward the deployment end 201 of the suture 200, eyelet 212 passes easily over the suture thread 202 and retainers 204 located thereon when the suture is pulled through eyelet 212 (or eyelet 212 is pulled over suture body 202) in the direction of deployment to decrease the circumference of variable loop 208.

Figure 3:
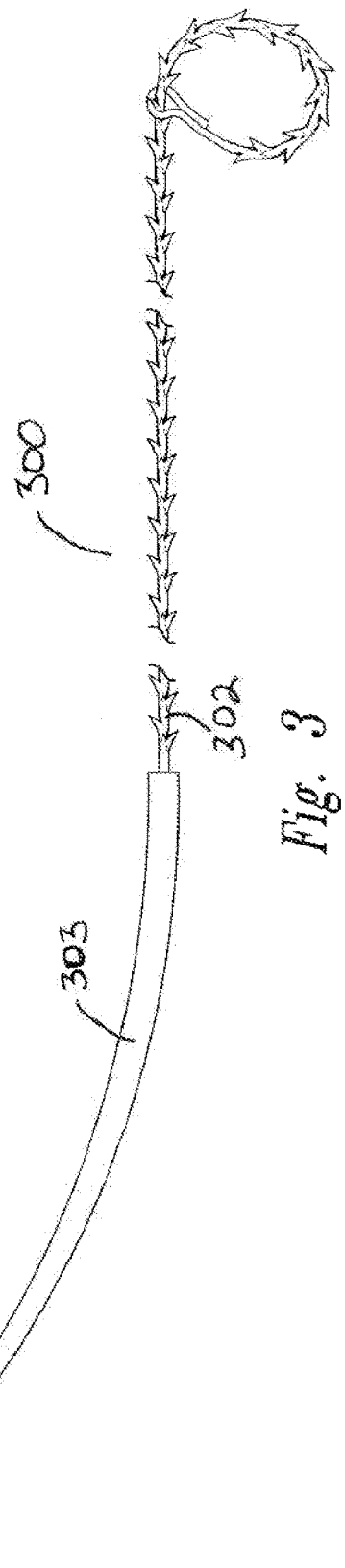
FIG. 3 is a view of a self-retaining variable loop suture in accordance with another embodiment of the present invention, having a needle at its deployment end.

As illustrated by comparison of FIG. 2 and FIG. 3, the deployment end of a suture 200 and 300, respectively, may be pointed. As shown in FIG. 2, the deployment end 201 may be pointed by converting the end of the suture body 202 into a sharp and rigid structure. Or, as illustrated in FIG. 3, the deployment end 301 may become pointed due to the attachment of a needle 303 to a terminus of the suture thread 302. FIG. 3 shows needle 303 at the deployment end 301 of variable loop suture 300.

In one embodiment, the invention provides a self-retaining system comprising a self-retaining suture as described herein including a deployment means. The self-retaining suture comprises a suture thread with a plurality of tissue retainers and one or more (usually only one is necessary) eyelets. The eyelet may be formed into a circular or generally circular shape, and in this shape the diameter of the eyelet can be measured in the usual way as the distance between any two opposing points (two points on opposite sides of the circle) on the inside of the eyelet. The needle diameter may be selected in view of the eyelet diameter. For example, the needle diameter may be larger than the eyelet diameter, for example, the needle diameter may be at least 5% greater, or at least 10% greater, or at least 15% greater or at least 20% greater than the eyelet diameter. In this example, a fixed loop is formed when the deployment end of the suture body passes through the eyelet and then the deployment end of the suture is attached to a suture needle. Since the suture needle has a diameter that is greater than the eyelet diameter, the deployment end of the suture cannot be taken back through the eyelet without breaking the eyelet and/or the needle, unless the eyelet is made of a flexible material which can stretch. The suture body of the invention typically does not stretch to any appreciable extent. Thus, the loop may be seen as being a fixed loop. In another example, the needle diameter is approximately the same as the eyelet diameter, in other words, the needle diameter is plus/minus 5% of the eyelet diameter, or in another embodiment, plus/minus 10% of the eyelet diameter. In this case, the needle diameter and the eyelet diameter are approximately the same, and it will be difficult or impossible to pull the deployment end of the suture back through the eyelet, after the deployment end has been attached to a needle. In another example, the needle diameter is chosen to be less than the eyelet diameter, such as where the needle diameter is less than 90% of the eyelet diameter, or less than 80%, or less than 70% or less than 60% or less than 50% of the eyelet diameter. In this case, the deployment end may be attached to a needle, and then the needle may be threaded through the eyelet. This option provides greater flexibility in forming the variable looped suture.

The needle diameter is typically chosen to be at least the same as the suture diameter, and in various embodiments the needle diameter is at least 110%, or at least 120%, or at least 130%, or at least 140%, or at least 150% of the suture thread diameter.

Figure 4A:
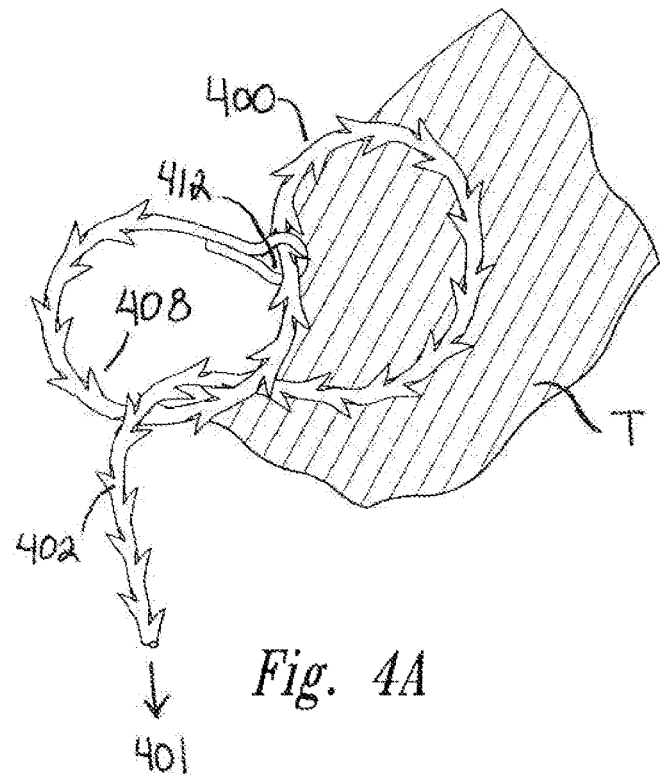
FIGS. 4A and 4B is a method of using a self-retaining variable loop suture in accordance with an embodiment of the present invention.
Figure 4B:
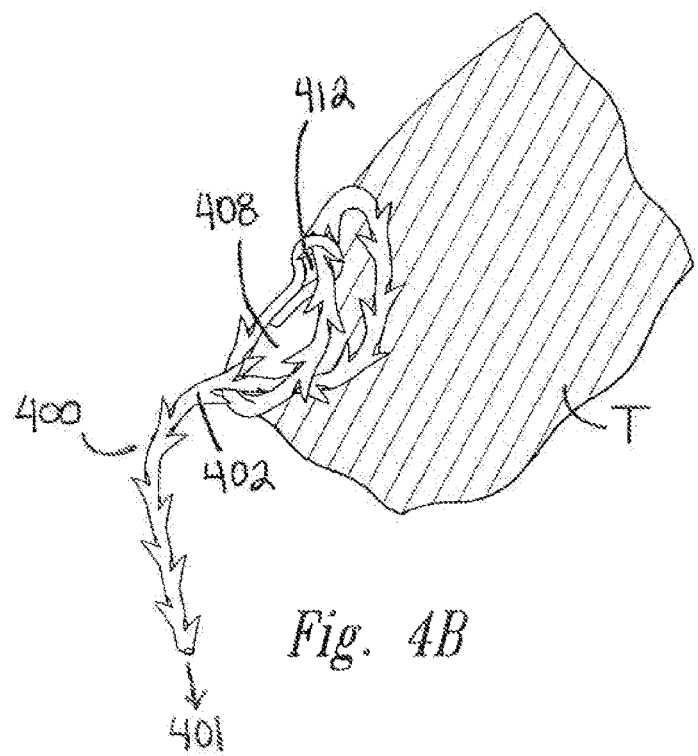

Use of self-retaining variable loop sutures of the present invention is illustrated in FIGS. 4A and 4B. In those drawings, suture 400 is drawn in a first stitch through tissue (indicated as a hatched region, "T"), and then elongated body 402 is drawn through the variable loop 408. When suture 400 is then pulled in the direction of the deployment end 401 (indicated with an arrow), suture body 402 continues to pass through loop 408, tensioning the variable loop and decreasing its size as it passes through eyelet 412. The suture is thus anchored and ready for continued deployment through tissue.

In one embodiment, the invention provides a method of suturing, where this method comprises: (a) providing a self-retaining system comprising a suture needle attached at an end of a self-retaining suture, the self-retaining suture comprising a suture thread having a thread diameter, a plurality of tissue retainers and an eyelet, where the suture thread passes through the eyelet to form a variable loop having an original diameter; (b) inserting the needle into the tissue of a patient at a first tissue location; (c) withdrawing the needle from the tissue of the patient at a second tissue location; (d) passing the needle and at least some of the suture thread through the variable loop; and (e) inserting the needle into the tissue of the patient at a third tissue location. Optionally, one or more of the following statements may be used in combination with a statement providing a method of suturing as provided herein: the suture thread is passed through the variable loop while simultaneously the diameter of the variable loop is decreased where optionally the decrease is greater than 50% of the original variable loop diameter; the diameter of the variable loop is decreased to provide a variable loop diameter that is less than 10 times the thread diameter; the diameter of the variable loop is decreased until the variable loop fits snugly around the suture thread; the suture thread is passed through the variable loop until the eyelet, the variable loop and the suture body together form an anchor on the tissue, and where further movement of the suture thread in the direction of the suture needle is resisted by the anchor.

In another embodiment, the invention provides a method of suturing tissue, the method comprising: (a) providing a suture thread attached to a suture needle, a portion of the suture thread forming a loop having an adjustable circumference; (b) threading the needle through the loop; and (c) deploying the needle through tissue of a patient and approximating the tissue with the suture thread. Optionally, one or more of the following statements may be used in combination with a statement providing a method of suturing as provided herein: the loop comprises suture thread and a fixed loop (also referred to as an eyelet), the fixed loop having an opening through which the suture thread passes to thereby form the loop having an adjustable circumference; the fixed loop (also referred to herein as the eyelet) and any means by which the fixed loop is formed or attached to the suture thread, all lie on a surface of the tissue after the tissue has been completely approximated; the circumference of the variable loop is adjusted to a desired value prior to threading the deployment end or needle through the variable loop; the circumference of the variable loop is adjusted to a desired value after threading the deployment end or needle through the variable loop; the circumference of the loop is adjusted to a desired value in the range, where that desired range may be 0.5 to 3 inches or 0.5 to 2 inches, or 0.5 to 1 inch, depending on the custom of the clinician and the nature of the wound that is being sewn; the circumference of the loop is reduced to a desired value, i.e., a value desired by the clinician as appropriate for his or her comfort and the wound being sewn; the needle is passed into and then out of tissue at first and second locations, respectively, prior to being threaded through the variable loop; the suture thread comprises tissue retainers; the suture thread comprises cuts in the suture thread, the cuts forming the tissue retainers, in other words, the cut provides a separation between suture thread material on either side of the cut, where the portion of suture thread material nearer the periphery of the suture thread may be pulled up and away from the suture thread on the other side of the cut, to thereby form a structure which is a tissue retainer; a cut made in the suture thread lies in a single plane, or in two planes such as where the angle of the cut is changed during the process of forming the cut in the suture thread, e.g., the first cut into the suture is relatively deep while the cut after the first cut is not (or not very) deep; a cut is made into the suture thread so as to provide a barb; tissue retainers are present on that portion of the suture thread that forms the loop having an adjustable circumference; tissue retainers are absent from a portion of the loop having an adjustable circumference.

In another embodiment, the invention provide a method of suturing that includes forming an anchor at a location on tissue of a patient, the method comprising: (a) providing a suture thread with an eyelet, the suture thread attached to a suture needle at a deployment end of the suture thread; (b) deploying the suture needle into tissue at the location, and then withdrawing the suture needle from tissue at an exit point; (c) passing the needle through a loop comprising suture thread, the loop having a variable circumference; (d) applying tension to the suture thread by pulling on the deployment end of the suture thread; (e) to thereby provide an anchor on top of the tissue, the anchor comprising the eyelet, the loop and a portion of the suture thread, the anchor resisting movement of the suture thread in the direction of the deployment end of the suture thread. Optionally, one or more of the following statements may be used in combination with a statement providing a method of suturing as provided herein: the loop comprises suture thread and a fixed loop (also referred to as an eyelet), the fixed loop having an opening through which the suture thread passes to thereby form the loop having an adjustable circumference; the fixed loop (also referred to herein as the eyelet) and any means by which the fixed loop is formed or attached to the suture thread, all lie on a surface of the tissue after the tissue has been completely approximated; the circumference of the variable loop is adjusted to a desired value prior to threading the deployment end or needle through the variable loop; the circumference of the variable loop is adjusted to a desired value after threading the deployment end or needle through the variable loop; the circumference of the loop is adjusted to a desired value in the range, where that desired range may be 0.5 to 3 inches or 0.5 to 2 inches, or 0.5 to 1 inch, or at least 0.5 inches, or at least 1 inch, or at least 1.5 inches, depending on the custom of the clinician and the nature of the wound that is being sewn; the circumference of the loop is reduced to a desired value, i.e., a value desired by the clinician as appropriate for his or her comfort and the wound being sewn; the needle is passed into and then out of tissue at first and second locations, respectively, prior to being threaded through the variable loop; the suture thread comprises tissue retainers; the suture thread comprises cuts in the suture thread, the cuts forming the tissue retainers, in other words, the cut provides a separation between suture thread material on either side of the cut, where the portion of suture thread material nearer the periphery of the suture thread may be pulled up and away from the suture thread on the other side of the cut, to thereby form a structure which is a tissue retainer; a cut made in the suture thread lies in a single plane, or in two planes such as where the angle of the cut is changed during the process of forming the cut in the suture thread, e.g., the first cut into the suture is relatively deep while the cut after the first cut is not (or not very) deep; a cut is made into the suture thread so as to provide a barb; tissue retainers are present on that portion of the suture thread that forms the loop having an adjustable circumference; tissue retainers are absent from a portion of the loop having an adjustable circumference.

To serve the purpose of allowing a clinician to identify and differentiate the eyelet, a market may be placed in the vicinity of the eyelet. The marker should be readily recognized and distinguished by the physician under the conditions in which the suture is to be used. For example, in microsurgery applications, markers may be used that are visible under the microscope, but not necessarily visible to the naked eye. Likewise in endoscopic applications, markers should used be that are visible through the endoscope and associated display system. If the suture will be used with fluoroscopic visualization then the markers may include radiopaque markers. If the suture will be used with ultrasound visualization then the markers may include echogenic markers. Thus, different markers and different types of markers may be appropriate under different circumstances depending upon the circumstances of the procedure and the scanning/imaging/visualization technology utilized in the procedure.

Markers can include different colors such as red, green, orange, yellow, green, blue etc. In some cases it may be desirable to use a color for markers that is uncommon in the operative environment. For example, it may be desirable to use green markers because green is not common in the human body. In endoscopic applications using green is advantageous because the video system can be programmed to emphasize green and enhance marker visualization without interfering with the remainder of the image.

The markers can be formed by various conventional methods. For example, the markers can be coated, sprayed, glued, dyed, stained, or otherwise affixed to the self-retaining suture systems or components thereof. Traditional colourant application processes include, without limitation, dipping, spraying (by, for example, an ink jet), painting, printing, applying and/or coating colourants on the suture section of interest. Critical fluid extraction (such as carbon oxide) may also be used to add colourant locally to all or part of the section desired to be marked. Alternatively, colourant(s) for the suture section of interest may be included in a portion of the suture material that is used to form the suture body, wherein that portion is in the section of interest of the manufactured suture.

Additionally, the suture section of interest can be demarcated by using an energy-activated colourant. For example, when a laser-activated colourant (that is, a pigment or dye which permanently changes colour after being exposed to laser energy) is used to colour the suture, then the eyelet or other suture section of interest can be demarcated by using laser energy to permanently change the suture coating in the suture section of interest. This also applies to using other energy activated colourants which are activated by other energy sources such as, but not limited to, heat, chemicals, microwaves, ultraviolet light, or x-rays. For example, bleaching chemicals such as sodium hypochlorite or hydrogen peroxide will permanently change the colourant's colour which allows for the demarcation of the eyelet or other region of the suture.

Additionally, the colourant(s) employed for demarcating the suture section of interest may be included on a plastic biocompatible material which is applied on the suture at the section of interest. Such a layer may be absorbable, such as a polyglycolide coating which has a colourant to mark the suture section of interest, or it may be a non-absorbable material, such silicone. The coloured material may be synthetic or may be derived from a natural source (whether the material be modified or unmodified), such as collagen. The plastic biocompatible material may be applied to the suture before or after the retainers are formed on the suture body.

Alternatively, the eyelet or other suture region may be reverse-marked, such that where the suture body is already visibly coloured, the colourant may be absent from all or part of the suture section of interest such that at least a portion of the section of interest is optically distinguishable by the surgeon from the rest of the suture. Such a suture may manufactured by including a colourant-free portion of suture material in the suture section of interest area during the manufacture of the suture body (for example, by extrusion) or by removal of colourant from the suture section of interest after the suture body has been manufactured, whether before or after retainers have been formed on the suture body. Colourant may be removed locally by, for example, critical fluid extraction such as (e.g., carbon oxide). It is not necessary to remove all of the colourant from the section of interest of the suture as long as there is a difference detectable by a surgeon between the section of interest and the rest of the suture.

Another example of a reverse-marked suture is one that lacks a coloured layer that is present on the rest of the suture body. A plastic biocompatible material bearing a colourant may be applied on the other sections of the suture, and at least where the other sections border the section of interest. Examples of such materials are discussed above. As in the foregoing examples, demarcating the suture section of interest may be effected in the suture manufacturing process either before or after forming retainers.

Another example of a reverse-marked suture is one having a coaxial structure wherein each coaxial layer having a different colour, and a portion of the outermost layer(s) is removed to visually expose a layer below. For example, a dual-layer monofilament polypropylene suture can be produced with a white inner core (intercoaxial layer) with a blue outer coaxial layer, and portions of the outer layer can be removed to visually expose the white inner monofilament to mark the suture section of interest.

Yet another example of a reverse-marked suture is one in which an external coating is removed (or partially removed) from the suture in the suture section of interest, and where either the coating or base suture has a contrasting colour difference. This technique of removing (or partially removing) material in the suture section of interest may also create a tactile demarcation of the suture section of interest.

The marking may include a radio-detectable compound or magnetic resonance imaging detectable compound. For example the suture section of interest provided with barium sulfate (BaSO4), such as by impregnating the suture with barium sulfate or adding a coating containing barium sulfate, will be detectable by electromagnetic energy. In the case of x-ray detection, the barium sulfate marked section of interest would be radiopaque. Likewise, computed tomography (CT) scans or computed axial tomography (CAT) scans can be used to detect the radio detectable section of interest. The use of electromagnetic energy for radio detection of the transition section is not limited to using x-ray wavelengths as other radio frequencies may be used. Likewise, gadolinium (Gd) or gadolinium compounds can be used for the marking of the suture section of interest especially when the detection will be done by using magnetic resonance imaging (MRI). The use of radio detectable or magnetic resonance imaging detectable marking may be useful to the surgeon during laparoscopic surgical procedures.

Figure 5A:
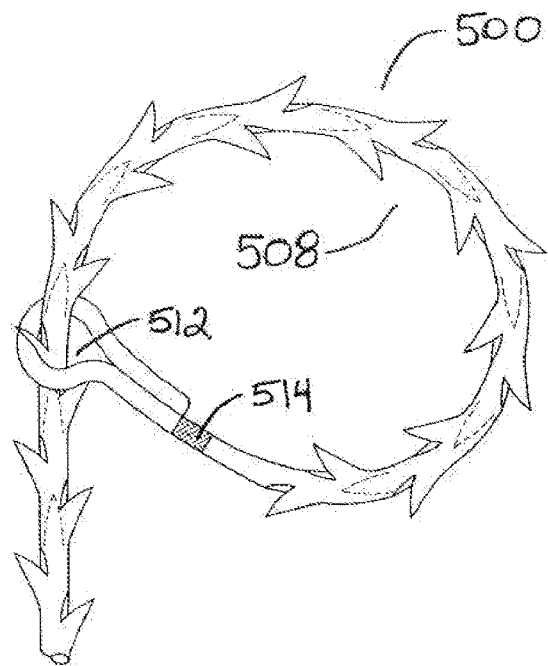
FIG. 5A is a view of the variable loop portion of a self-retaining suture in accordance with an embodiment of the invention, illustrating a visible demarcation of the fixed loop.
Figure 5B:
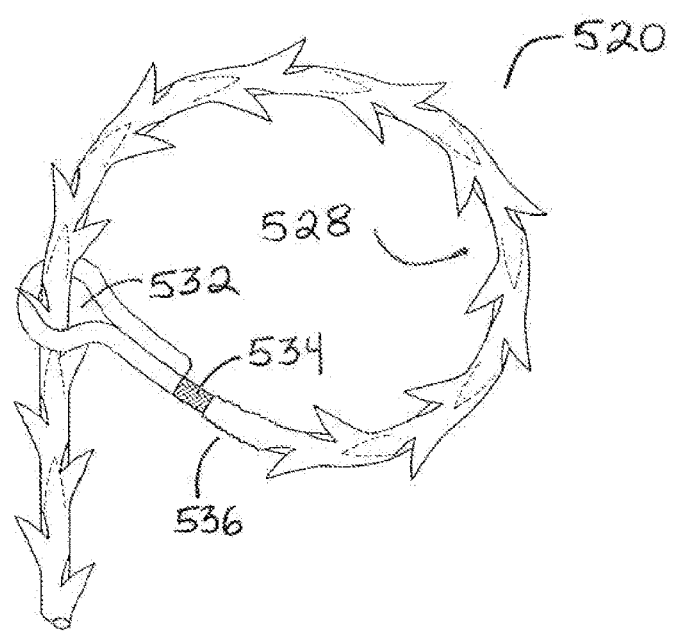
FIG. 5B is a view of the variable loop portion of a self-retaining suture in accordance with an embodiment of the invention, illustrating a surface feature of embodiment.

The region of the variable loop at the base of the eyelet may be marked to increase its visibility to the clinician, either for the purpose of indicating where it is during suture deployment, or to allow the clinician to identify where the anchor is in order to sever it for the purpose of removing the deployed suture from the tissue. FIGS. 5A, 5B, 5C, and 5D illustrate the trailing ends of variable loop sutures having such markings. In FIG. 5A, variable loop 508 of suture 500 includes eyelet 512, which is marked at its base 514. Suture 520 of FIG. 5B includes a variable loop 528 having demarcation 534 near eyelet 532 in addition to a surface feature 536 adjacent to the eyelet base 534 where feature 536 provides a different tactile feeling to the suture 520 compared to other locations on the suture, while suture 540 of FIG. 5C has a variable loop 548 having demarcation 554 near eyelet 552, and suture 560 of FIG. 5D shows a variable loop 568 having two demarcations 534 near eyelet 572 and demarcation 576 located elsewhere on the variable loop 568.

In some embodiments, the suture may additionally be provided with a surface feature for some portion of the suture body adjacent to the fixed loop, in order to provide some resistance, perceptible to the clinician, to the variable loop being pulled all the way to the fixed loop. While in some of these embodiments it is not necessary for the surface feature to prevent the variable loop from being tightened all the way to the fixed loop, in yet other embodiments the surface feature may function to do just that. Some examples, without limitation, of suitable surface features are dimpling, rippling, corrugation, roughening, serrations, ridges, filaments, so forth. In this connection, FIG. 5B includes surface feature 536 near eyelet 532. Of course, these surface features may also take the form of a short segment retainers oriented away from the suture deployment end, which would resist the movement of the suture body through the eyelet, The latter may be of the same pattern as the balance of the suture or may be different, i.e., a short segment of retainers having the same or different configuration as the plurality of barbs oriented to the deployment end.

Figure 5C:
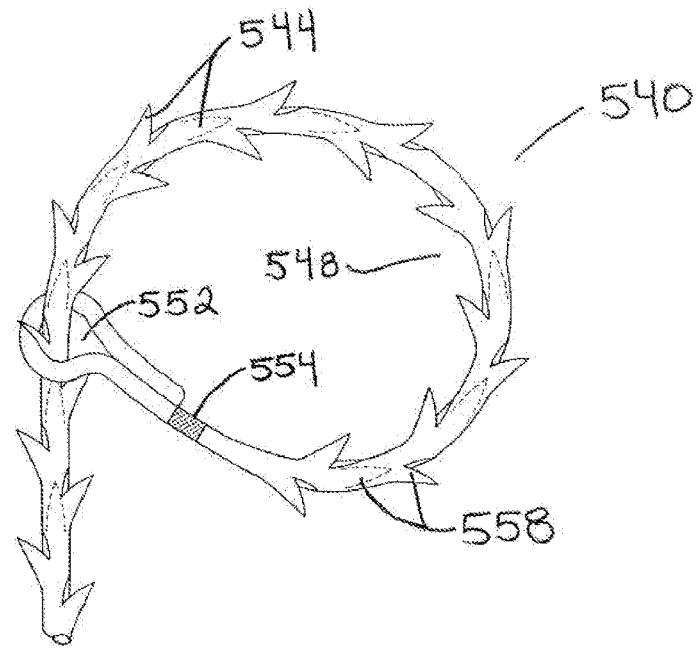
FIG. 5C is a view of the variable loop portion of a self-retaining suture in accordance with an embodiment of the invention, illustrating a surface feature of that embodiment.
Figure 5D:
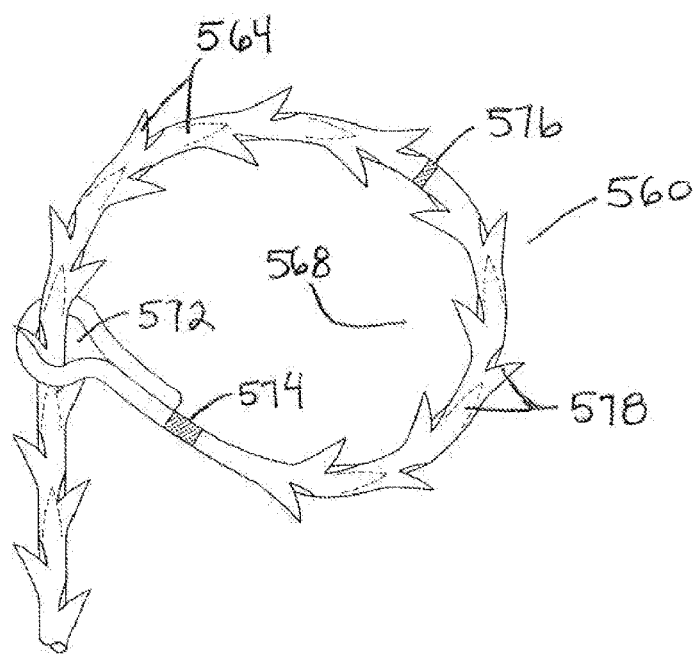
FIG. 5D is a view of the variable loop portion of a self-retaining suture in accordance with an embodiment of the invention, illustrating a surface feature of that embodiment.

In FIG. 5C, retainers 544 oriented toward the deployment end of the suture pass easily through eyelet 552, while retainers 558 are oriented in the opposite direction and so somewhat resist having the eyelet drawn over them. Similarly, suture 560 of FIG. 5D is provided with retainers 564 oriented toward the deployment and retainers 578, which are oppositely oriented. Suture 560 is also provided with an additional marking 576 in between the two sets of retainers, in order to allow the clinician to identify the region between the two sets.

Figure 6A:
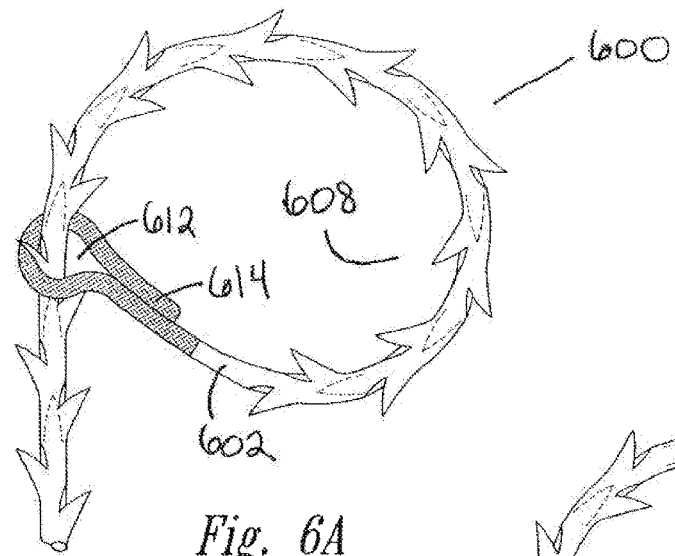
FIG. 6A is a view of the variable loop portion of a self-retaining suture in accordance with an embodiment of the invention, illustrating a visible demarcation of the fixed loop of that embodiment.

Referring now to FIG. 6A, this provides a view of the variable loop portion 608 of a self-retaining suture 600 in accordance with an embodiment of the invention, illustrating a visible demarcation 614 of the fixed loop of that embodiment. In other words, the fixed loop (alternatively referred to as the eyelet) has a different surface appearance or a different surface tactile feel in comparison to the adjoining suture thread. In FIG. 6A, the eyelet 612 is constructed from a darker colored material than the material that forms the adjoining suture thread 602. Alternatively, the eyelet could be formed from a lighter colored material, or a totally different colored material than the adjoining suture thread. The eyelet might be formed of material having a matt finish while the adjoining suture thread had a natural or shiny appearance. The eyelet may also, or alternatively, be formed of materials that contain grooves or other indentations or ridges that are not present on the adjoining suture thread, which provides a tactile distinction between the eyelet region and the adjoining suture thread. With this visible demarcation between the eyelet and the adjoining suture thread, the clinician who uses the suture, or perhaps a robot that handles the suture, can more readily see the eyelet and distinguish the eyelet from the adjoining suture thread.

Figure 6B:
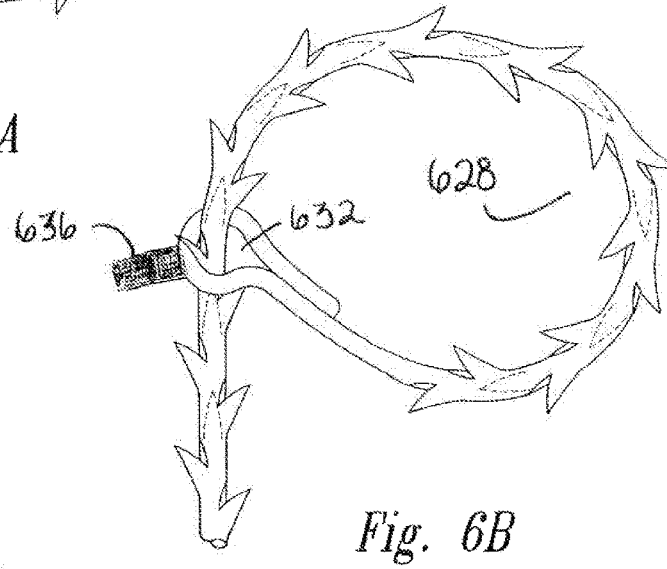
FIG. 6B is a view of the variable loop portion of a self-retaining suture in accordance with another embodiment of the invention, illustrating a grasp engagement element of that embodiment.
Figure 6C:
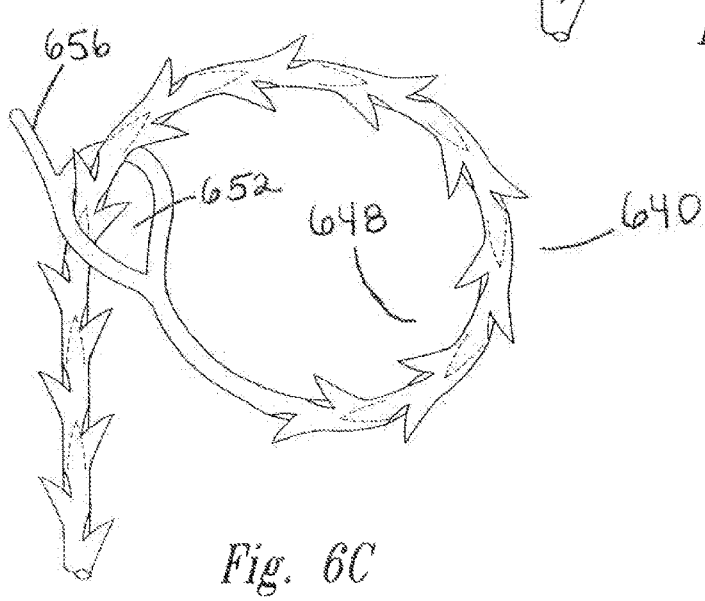
FIG. 6C is a view of the variable loop portion of a self-retaining suture in accordance with yet another embodiment of the invention, illustrating a grasp engagement element of that embodiment.

Referring now to FIGS. 6B and 6C, the eyelet may be provided with or be in combination with a grasp engagement element, to facilitate the removal of the anchor from the suture if it is decided that the suture is to be removed from the tissue. As shown in FIG. 6B, suture 620 having variable loop 628 with an eyelet 632 and an attachment region 634 has a tab 636 as the grasp engagement element, while suture 640 of FIG. 6C includes a length of unbarbed suture material 656 as a grasp engagement element located on or as part of the integrally-formed eyelet 652 of variable loop 648. Grasp engagement elements 636 and 656 illustrate two options for a feature that is part of, or is attached to the eyelet and is of a size and orientation which can readily be grasped or grabbed or gripped or held by the health care professional as a means of lifting the eyelet and associated anchor away from the tissue. A grasp engagement element is an optional feature of each of the variable loop sutures described herein.

The grasp engagement element can be made from either or both absorbable or non-absorbable materials. For example, a non-absorbable grasp engagement element made from polyester felt or polytetrafluoroethylene felt can be used to allow the surgeon to find and gently pull the eyelet to facilitate removal of the anchor from the suture body if and when it is desired to remove the suture from tissue (by detaching the anchor and then pulling the suture out from its deployment end). Examples of absorbable materials include glycolide and glycolide-lactide polymers. The use of an absorbable grasp engagement element can be especially useful for deep cavity tissue closures where the surgeon may wish to have a choice of whether or not to leave the grasp engagement element inside the body. Additionally, the grasp engagement element can be coloured (as shown by the shading of tab 636 of FIG. 6B) to improve the visibility of the element. This includes, but is not limited to, using fluorescent colourants, radio detectable compounds, or magnetic resonance imaging detectable compounds.

Manufacturing and Materials

Suture threads described herein may be produced by any suitable method, including without limitation injection moulding, stamping, cutting, laser, extrusion, and so forth. With respect to cutting, polymeric thread or filaments may be manufactured or purchased for the suture body, and the retainers can be subsequently cut onto or into the suture body; they may be hand-cut, laser-cut, or mechanically machine-cut using blades, cutting wheels, grinding wheels, and so forth. The sutures may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues. As are appropriate to the indication or use of the suture in question, the sutures may be provided with retainers of various configurations, arrangements, densities, and so forth, such as those taught in publications referenced herein.

Variable loops for sutures of the present invention may be formed in several ways. Referring to the suture 700 shown in FIG. 7, variable loop 708 includes eyelet 712 through which suture body 702 passes. Eyelet 712 is formed by passing what would otherwise be the non-deployment terminus 791 of suture body 702 around and back upon itself and attaching it externally to the suture body 702 at attachment region 714. In this case, the attachment region 714 is adjacent to the eyelet 712. In contrast, and referring to the suture 800 shown in FIG. 8 which illustrates eyelet 812 of variable loop 808 formed from the trailing end (alternatively referred to as the non-deployment end) 891 of suture body 802 on an internal attachment, that is, the attachment region 814 is inside and is part of the structure that forms the eyelet. The attachments mentioned in reference to these figures may be made to have a permanent nature by welding, gluing, and so forth.

Noteworthy is that the non-deployment end of the suture thread need not have any particular shape or appearance or function when it is located in the attachment region. Since neither the eyelet nor the adjacent attachment region of the variable loop sutures of the present invention are intended to enter tissue, there is no need to facilitate the entry of, e.g., the attachment region by providing any particular shape that would facilitate such entry. For example, the end or tip of the non-deployment end of the sutures of the present invention may be squared off compared to the sides of the adjacent suture thread, rather than having an angle or slant that would facilitate entry into tissue. The deployment end may, in fact, be designed or adapted to retard entry of the attachment region into tissue. This is particularly relevant when the eyelet is formed by having the attachment region located adjacent to the eyelet. This same issue is not relevant if the attachment region is part of the material that forms the eyelet.

Alternatively, the eyelet 912 may be integral to the suture body 902 as is shown by the suture 900 illustrated in FIG. 9, in which eyelet 912 of variable loop 908 is continuous with suture body 902. Thus, in this embodiment, there is no attachment region.

As a further alternative embodiment, the eyelet may be formed independently from the suture thread, and then the eyelet is joined to the suture thread at a suitable location. For example, the non-deployment end of the suture thread may be tied to an eyelet, in the same manner as the end of a rope can be tied to a ring. In this alternative embodiment, it is desirable that the joining together of the suture thread and the eyelet be done in a secure manner, so that the eyelet does not become separated from the suture thread at an inopportune time. A secure joining of the eyelet and the suture thread may be accomplished, for example, by welding the knot which is used to tie the eyelet to the suture thread. As another example, the eyelet may take the form of a ring (or polygon or other suitable shape defining a hole through which the suture thread may pass or be threaded) where the ring has a hole through which the suture thread may pass in order to secure the ring to the suture thread. For instance, after passing through this hole, the non-deployment end of the suture thread may be formed into a knot of such a size that it cannot easily pass through the hole. In this way, the suture thread is secured to an eyelet. As a final example, the eyelet may be securely joined to a feature where the feature is readily secured to the suture thread. For instance, two rings joined in the shape of a FIG. 8, the two rings not necessarily being of the same diameter, provides a structure where the suture thread may be tied to one ring, while the adjoining ring is available to serve as the eyelet. Rather than having the eyelet joined to a ring, the eyelet may be joined to a tab which can be folded and crimped around the suture thread. The eyelet might alternatively be joined to a hollow cylinder, where the non-deployment end of the suture thread may be inserted into the cylinder, and then the cylinder is crimped to secure the suture thread within the cylinder (in a like manner to the well known way in which the deployment end of a suture is swaged to a needle, but in this case the non-deployment end of a suture thread would be swaged to an eyelet). Having the eyelet formed separately from the suture thread provides for greater flexibility (i.e., independence) in selecting materials from which to form the suture thread and the eyelet.

The dimensions of the eyelet may be varied; for example, the inner transverse length of the eyelet (that is, the longest inner dimension across the eyelet) may be as small as about the transverse length of the suture body cross section (that is, the longest dimension across the suture body cross section, regardless of the shape of the cross section) and as large as about four times or even ten times the transverse length of the suture body cross section. Other ranges for the inner transverse length that may be suitable are one-and-a-half times the transverse length of the suture cross section to about ten times transverse length of the suture cross section, one-and-a-half times the transverse length of the suture cross section to about four times transverse length of the suture cross section, or about twice the transverse length of the suture cross section to about three times the transverse length of the suture cross section.

After preparation, the self-retaining suture system may be packaged for ease of storage, handling and use. Suitable packaging systems are known in the art, where exemplary suture packages are described in U.S. Patent Publication Nos. 20110056859, issued as U.S. Pat. No. 8,459,446 on Jun. 11, 2013 and 20100230300, now abandoned. Before, but preferably after the packaging process, the suture may be sterilized by, e.g., radiation.

In one embodiment there is provided a method of making a self-retaining suture system, the method comprising (a) providing a suture thread, the suture thread comprising a deployment end and either comprising or being attached to an eyelet, (b) forming a plurality of cuts in the suture thread to provide a plurality of tissue retainers; (c) threading the deployment end of the suture thread through the eyelet to thereby form a loop of variable circumference; (d) threading the deployment end of the suture through the loop of variable circumference to provide a suture ready for packaging; (e) placing the suture ready for packaging into a package suitable for storing the suture and suitable for allowing a health care worker to readily access the suture ready for packaging. One or more of the following statements may be used in combination with the description of a method of making a self-retaining suture system, to further describe and state the invention: the method further comprises attaching a suture needle to an end of the suture thread, where optionally the needle is attached to the suture thread after the end of the suture thread has been threaded through the eyelet or the needle is attached to the suture thread after the end of the suture thread has been threaded through the loop of variable circumference; the suture thread is sterilized; the eyelet is integrally formed with the suture thread; the eyelet is attached to the suture thread; the eyelet is formed by (a) folding a non-deployment end of the suture thread, also referred to as the trailing end of the suture thread, back upon a portion of the suture thread to provide for an attachment region, wherein the non-deployment end of the suture is in contact with the portion of the suture thread in the attachment region; and (b) adhering the non-deployment end and the portion of the suture thread in the attachment region to one another, where in such a case, the adhering may be achieved by welding together the non-deployment end and the portion of the suture thread in the attachment region or it may be achieved by gluing together the non-deployment end and the portion of the suture thread in the attachment region; the eyelet comprises the attachment region which will occur in the case where the deployment end is folded back onto a portion of the suture thread that forms part of the eyelet; the eyelet is adjacent to the attachment region which will occur in the case where the deployment end is folded back onto a portion of the suture thread that does not form part of the eyelet but which is adjacent to the eyelet at the base of the eyelet.

Self-retaining sutures described herein may also incorporate materials that further promote tissue engagement. In addition to tissue engagement at the retainers, use of tissue engagement-promoting materials in at least part of the suture bodies (whether or not such materials also make up all or part of the retainers) can enhance the ability of the sutures to stay in place. One such class of tissue engagement-promoting materials are porous polymers that can be extruded to form suture bodies, including both microporous polymers and polymers that can be extruded with bubbles (whether bioabsorbable or nonbioabsorbable). A suture synthesized with such materials can have a three-dimensional lattice structure that increases tissue engagement surface area and permits tissue infiltration into the suture body itself, thus having a primary structure that promotes successful suture use. Moreover, by optimizing pore size, fibroblast ingrowth can be encouraged, further facilitating the suture to be anchored in the tissue.

One such microporous polymer is ePTFE (expanded polytetra-fluoroethylene). Self-retaining incorporating ePTFE (and related microporous materials) are well-suited to uses requiring a strong and permanent lift (such as breast lifts, face lifts, and other tissue repositioning procedures), as tissue infiltration of the suture results in improved fixation and engraftment of the suture and the surrounding tissue thus providing superior hold and greater longevity of the lift.

Additionally, self-retaining sutures described herein may be provided with compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) by inserting the suture into a sleeve or mesh which is comprised of, or coated with, a formulation, or (e) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumour excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for their synergistic effects.

Clinical Uses

In addition to the general wound closure and soft tissue repair applications described in the preceding sections, self retaining sutures can be used in a variety of other indications.

Self-retaining sutures described herein may be used in various dental procedures, i.e., oral and maxillofacial surgical procedures. The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures. Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. They may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self retaining sutures can be used in a variety of veterinary applications for a wide number of surgical and traumatic purposes in animal health.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims. Some specific embodiments of the invention are:

A self-retaining suture comprising: a first end for penetrating tissue; an elongated suture body (which may alternatively be referred to as a suture thread), having a periphery; a first plurality of retainers on the periphery of the elongated body (which may alternatively be referred to as a suture thread or suture body) and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a variable loop of variable circumference, wherein the variable loop includes a fixed loop (which may alternatively be referred to as an eyelet) slidably engaging the elongated body for slidingly varying the circumference of the variable loop, and wherein the first end may pass through the variable loop to secure tissue as an anchor, the anchor preventing movement of the suture in the direction of deployment of the first end. Optionally, one or more of the following statements may be used to further describe a self-retaining suture provided herein: the first end is adapted to penetrate tissue; the first end is attached to a needle; the suture further comprises a surface feature on at least some of the periphery of the elongated body between the fixed loop (eyelet) and the first plurality of retainers, the surface feature resisting sliding of the fixed loop over the surface feature, where optionally the surface feature comprises a second plurality of retainers, the second plurality of retainers being oriented away from the first end and/or the surface feature is disposed at least in part in the circumference of the variable loop; the elongated body has a cross section having a transverse length (tl) and the fixed loop has an inner transverse length (TL) and wherein the ratio of TL:tl is about 1:1 to about 10:1 or the ratio of TL:tl is about 1:1 to about 4:1 or the ratio of TL:tl is about 1:1 to about 3:1 or the ratio of TL:tl is about 1.5:1 to about 10:1 or the ratio of TL:tl is about 1.5:1 to about 4:1 or the ratio of TL:tl is about 2:1 to about 3:1; the fixed loop is attached to or further comprises a grasp engagement element; at least one of the retainers of the first plurality differs in configuration from other retainers of the first plurality; retainers of the second plurality differ in configuration from retainers of the first plurality; the fixed loop further comprises a visible marking; the cross section of the elongated suture body (alternatively called suture thread) is non-circular; the cross section of the elongated suture body is polygonal; the suture thread further comprises a therapeutic agent.

A self-retaining suture comprising: a first end for penetrating tissue; an elongated suture body (alternatively called a suture thread) having a periphery and a cross section, the cross section having a transverse length (tl); a first plurality of retainers on the periphery of the elongated body (alternatively called the elongated suture body or suture thread) and oriented to the first end, the first plurality of retainers yielding toward the suture body (alternatively called a suture thread) during movement of the suture through tissue in a direction of deployment of the first end, and resisting movement of the suture, when in tissue, in a direction substantially opposite the direction of deployment of the first end; a second end having a variable loop of variable circumference, wherein the variable loop includes a fixed loop (alternatively identified as an eyelet) slidably engaging the elongated body for slidingly varying the circumference of the variable loop, and wherein the first end may pass through the variable loop to secure tissue as a third, anchoring loop in tissue for preventing movement of the suture in the direction of deployment of the first end.

A self-retaining suture comprising: a first end for penetrating tissue; an elongated suture body having a periphery and a cross section, the cross section having a transverse length (tl); a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a slip knot, the slip knot comprising a loop of variable circumference through which the first end may pass to secure tissue as an anchor for preventing movement of the suture in the direction of deployment of the first end.

A self-retaining suture comprising: a first end for penetrating tissue; an elongated suture body having a periphery and a cross section, the cross section having a transverse length (tl); a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a slip knot, the slip knot comprising a loop of variable circumference through which the first end may pass to secure tissue as an anchoring loop in tissue for preventing movement of the suture in the direction of deployment of the first end.

A self-retaining suture comprising: a first end for penetrating tissue; an elongated suture body having a periphery and a cross section, the cross section having a transverse length (tl); a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; a second end having a variable loop of variable circumference, wherein the variable loop includes a fixed loop having an inner transverse length (TL) and slidably engaging the elongated body for slidingly varying the circumference of the variable loop, wherein the ratio of TL:tl is about 1:1 to about 10:1; wherein the first end may pass through the variable loop to secure tissue as an anchor for preventing movement of the suture in the direction of deployment of the first end.

We claim:

1. A self-retaining suture comprising:
   a. a needle having a first diameter;
   b. a suture comprising:
      i. a first end for penetrating tissue, wherein the first end is attached to the needle;
      ii. an elongated suture body having a periphery;
      iii. a first plurality of retainers on the periphery of the elongated body and oriented to the first end, the first plurality of retainers yielding toward the suture body during movement of the suture through tissue in a direction of deployment of the first end, and resisting movement of the suture, when in tissue, in a direction substantially opposite the direction of deployment of the first end; and
      iv. a second end having a variable loop of variable circumference, wherein the variable loop includes a fixed loop slidably engaging the elongated body for slidingly varying the circumference of the variable loop, wherein the fixed loop has no retainers on its surface and said fixed loop is formed by passing a non-deployment terminus of the suture body around and back upon itself and attaching said non-deployment terminus to the suture body such that said non-deployment terminus is located outside the interior of the fixed loop, wherein the fixed loop has a second diameter that is less than the first diameter that is configured to prevent the needle from passing through the fixed loop, and wherein the first end is configured to pass through the variable loop to secure tissue as an anchor, the anchor preventing movement of the suture in the direction of deployment of the first end.

2. The suture of claim 1, further comprising a surface feature on at least some of the periphery of the elongated body between the fixed loop and the first plurality of retainers, the surface feature resisting sliding of the fixed loop over the surface feature.

3. The suture of claim 1, wherein the elongated body has a cross section having a transverse length (tl) and the fixed loop has an inner transverse length (TL) and wherein the ratio of TL:tl is about 1:1 to about 10:1.

4. The suture of claim 1, wherein the fixed loop further comprises a grasp engagement element.

5. The suture of claim 1, wherein the fixed loop further comprises a visible marking.

6. The suture of claim 1, wherein the cross section of the elongated suture body is non-circular.

7. The suture of claim 1, further comprising a therapeutic agent.

8. The suture of claim 1, wherein the non-deployment terminus is secured to the suture body at an attachment region, and the attachment region is adjacent to the fixed loop.

9. The suture of claim 1, wherein the non-deployment terminus is secured to the suture body at an attachment region, and the attachment region is a welded site.

10. The suture of claim 1, wherein the non-deployment terminus is secured to the suture body at an attachment region, and the attachment region is a glued site.

11. The suture of claim 1, wherein the second end includes a surface feature disposed proximal to the fixed loop, wherein the surface feature is configured to provide a tactile indication.

12. The suture of claim 11, wherein the surface feature is selected from the group consisting of dimpling, rippling, corrugation, roughening, serrations, ridges, and filaments.

13. The suture of claim 1, wherein the fixed loop is enclosed forming a completely bounded perimeter such that the fixed loop does not open up to a portion of the variable loop.

14. The suture of claim 1, wherein the suture further comprises a second plurality of retainers on the periphery of the elongated body disposed within the variable loop, wherein the second plurality of retainers are oriented opposite the first plurality of retainers.

15. A method of suturing comprising:
   a. providing a self-retaining system comprising a suture needle and a self-retaining suture, the self-retaining suture comprising a suture thread having a thread diameter, a plurality of tissue retainers and an eyelet, said eyelet formed by passing a non-deployment terminus of the suture thread around and back upon itself and attaching said non-deployment terminus to the suture thread such that said non-deployment terminus is located outside the interior of the eyelet, where the suture thread passes through the eyelet to form a variable loop having an original diameter, wherein the suture needle is attached to an end of the self-retaining suture after the variable loop is formed, wherein the suture needle has a first diameter and the eyelet has a second diameter, wherein the second diameter is less than the first diameter to prevent the suture needle from passing through the eyelet;
   b. inserting the needle into the tissue of a patient at a first tissue location after passing the suture thread through the eyelet to form the variable loop;

c. withdrawing the needle from the tissue of the patient at a second tissue location;
d. passing the needle and at least some of the suture thread through the variable loop; and
e. inserting the needle into the tissue of the patient at a third tissue location.

16. The method of claim 15, wherein the suture thread is passed through the variable loop while simultaneously the diameter of the variable loop is decreased.

17. The method of claim 16, wherein the diameter of the variable loop is decreased until the variable loop fits snugly around the suture thread.

18. The method of claim 15, wherein the suture thread is passed through the variable loop until the eyelet, the variable loop and the suture body together form an anchor, and where further movement of the suture thread in the direction of the suture needle is resisted by the anchor.

19. A method of suturing comprising:
a. providing a self-retaining suture, the self-retaining suture comprising a suture thread having a thread diameter, a plurality of tissue retainers and an eyelet, said eyelet formed by passing a non-deployment terminus of the suture thread around and back upon itself and attaching said non-deployment terminus to the suture thread such that said non-deployment terminus is located outside the interior of the eyelet;
b. passing the suture thread through the eyelet to form a variable loop having an original diameter after providing the self-retaining system;
c. attaching a suture needle to an end of the self-retaining suture, wherein the suture needle has a first diameter and the eyelet has a second diameter, wherein the second diameter is less than the first diameter to prevent the suture needle from passing through the eyelet;
d. inserting the needle into the tissue of a patient at a first tissue location after passing the suture thread through the eyelet to form the variable loop;
e. withdrawing the needle from the tissue of the patient at a second tissue location; and
f. passing the needle and at least some of the suture thread through the variable loop.

20. The method of claim 19, further comprising:
inserting the needle into the tissue of the patient at a third tissue location after passing the needle and at least some of the suture thread through the variable loop.

* * * * *